(12) United States Patent
Strapoc et al.

(10) Patent No.: US 10,371,691 B2
(45) Date of Patent: Aug. 6, 2019

(54) SYSTEM AND METHOD FOR LOGGING ISOTOPE FRACTIONATION EFFECTS DURING MUD GAS LOGGING

(71) Applicant: Geoservices Equipements SAS, Roissy en France (FR)

(72) Inventors: Dariusz Strapoc, Paris (FR); Martin Niemann, Clamart (FR); Benjamin Jacquet, Paris (FR)

(73) Assignee: GEOSERVICES EQUIPEMENTS, Roissy en France (FR)

( * ) Notice: Subject to any disclaimer, the term of this patent is extended or adjusted under 35 U.S.C. 154(b) by 835 days.

(21) Appl. No.: 14/903,388

(22) PCT Filed: Jul. 10, 2014

(86) PCT No.: PCT/US2014/046134
§ 371 (c)(1),
(2) Date: Jan. 7, 2016

(87) PCT Pub. No.: WO2015/006552
PCT Pub. Date: Jan. 15, 2015

(65) Prior Publication Data
US 2016/0153955 A1    Jun. 2, 2016

(30) Foreign Application Priority Data
Jul. 10, 2013  (EP) .................................... 13305982

(51) Int. Cl.
*G01N 33/28* (2006.01)
*E21B 49/00* (2006.01)
(Continued)

(52) U.S. Cl.
CPC ....... *G01N 33/2823* (2013.01); *E21B 21/067* (2013.01); *E21B 47/10* (2013.01); *E21B 49/005* (2013.01); *G01N 33/0047* (2013.01)

(58) Field of Classification Search
CPC ........... G01N 33/2823; G01N 33/0006; G01N 2001/2267; G01N 2030/025; E21B 21/067; E21B 47/10; E21B 49/005; E21B 49/08
See application file for complete search history.

(56) References Cited

U.S. PATENT DOCUMENTS 3,899,926 A * 8/1975 Haden ................... E21B 49/005
73/152.04
4,635,735 A   1/1987 Crownover
(Continued)

FOREIGN PATENT DOCUMENTS

EP      1508794 A1    2/2005
WO   2004104639 A1   12/2004
(Continued)

OTHER PUBLICATIONS

International Search Report and Written Opinion issued in International App. No. PCT/US2014/046134 dated Nov. 6, 2014.
(Continued)

*Primary Examiner* — Maurice C Smith

(57) ABSTRACT

A mud gas analyzer and a well-site system using the mud gas analyzer are described. The mud gas analyzer includes at least one degasser adapted to extract gas from drilling mud passing through a flow path formed at least partially by a drill string within a well and an annulus positioned between an exterior surface of the drill string and a formation surrounding the well at a well-site, at least one gas analyzer adapted to interact with the gas extracted from the drilling mud. The gas analyzer determines an isotopic composition of a gas liberated from the drilling mud and generates a sequence of signals indicative of ratios of isotopes of a gas species liberated from the drilling mud. The computer system includes a processor adapted to execute logic to cause the processor to access information indicative of the
(Continued)

well's and drilling tools geometry and mud flow rates or access information from any other source providing particular locations of the well at which mixing of fractions of a gas species occurred including formation gas and recycled gas, receive the sequence of signals, and to calculate and log isotopic characteristics of the gas species entering the drilling mud at particular locations of the well within a geological formation.

17 Claims, 11 Drawing Sheets

(51) Int. Cl.
*G01N 33/00* (2006.01)
*E21B 21/06* (2006.01)
*E21B 47/10* (2012.01)

(56) References Cited

U.S. PATENT DOCUMENTS

| | | | |
|---|---|---|---|
| 4,860,581 A | 8/1989 | Zimmerman et al. | |
| 4,887,464 A * | 12/1989 | Tannenbaum | E21B 21/08 |
| | | | 73/152.04 |
| 4,936,139 A | 6/1990 | Zimmerman et al. | |
| 6,301,959 B1 | 10/2001 | Hrametz et al. | |
| 6,443,001 B1 | 9/2002 | Duriez et al. | |
| 6,585,045 B2 | 7/2003 | Lee et al. | |
| 6,609,568 B2 | 8/2003 | Krueger et al. | |
| 6,670,605 B1 * | 12/2003 | Storm, Jr. | E21B 49/08 |
| | | | 250/255 |
| 6,719,049 B2 | 4/2004 | Sherwood et al. | |
| 7,032,444 B2 | 4/2006 | Breviere et al. | |
| 7,529,626 B1 | 5/2009 | Ellis | |
| 8,838,390 B1 * | 9/2014 | Selman | E21B 44/00 |
| | | | 166/264 |
| 2004/0000433 A1 | 1/2004 | Hill et al. | |
| 2004/0014223 A1 | 1/2004 | Audibert et al. | |
| 2006/0224333 A1 | 10/2006 | Frechin et al. | |
| 2006/0249288 A1 | 11/2006 | Drozd et al. | |
| 2008/0147326 A1 | 6/2008 | Ellis | |
| 2009/0199618 A1 | 8/2009 | Evrard | |
| 2011/0139464 A1 * | 6/2011 | Henderson | E21B 21/01 |
| | | | 166/370 |
| 2013/0087698 A1 | 4/2013 | Pomerantz et al. | |

FOREIGN PATENT DOCUMENTS

| | | |
|---|---|---|
| WO | 2008017949 A1 | 2/2008 |
| WO | 2009037517 A2 | 3/2009 |

OTHER PUBLICATIONS

Extended European Search Report issued in European App. No. 13305982.4 dated Jan. 20, 2014.
Bernard et al., "Light hydrocarbons in recent Texas continental shelf and slope sediments," J. Geophys. Res., 83(C8), 4053-4061, Aug. 20, 1978.
Berner et al., "Maturity related mixing model for methane, ethane and propane, based on carbon isotopes," Org. Geochem., vol. 13, Nos. 1-3, pp. 67-72, 1988.
Faber et al., "Gaseous hydrocarbons of unknown origin found while drilling," Org. Geochem., vol. 13, Nos. 4-6, pp. 875-879, 1988.
McKinney et al., "Advanced Mud Gas Logging in Combination with Wireline Formation Testing and Geochemical Fingerprinting for an Improved Understanding of Reservoir Architecture," SPE 109861 presented at 2007 SPE Annual Technical Conference and Exhibition, Anaheim, California, Nov. 11-14, 2007.
Schoell, "Genetic Characterization of Natural Gases," American Association of Petroleum Geologists Bulletin, 67(12), 2225-2238, 1983.
Uehara et al., "Isotope analysis of environmental substances by a new laser-spectroscopic method utilizing different pathlengths," Sensors and Actuators B 74, pp. 173-178, 2001.
Wenger et al., "Drill-Bit Metamorphism: Recognition and Impact on Show Evaluation," SPE 125218 presented at the 2009 SPE Annual Technical Conference and Exhibition held in New Orleans, Lousiana, Oct. 4-7, 2009.
Whiticar, "Carbon and hydrogen isotope systematics of bacterial formation and oxidation of methane," Chemical Geology 161, pp. 291-314, 1999.

* cited by examiner

SYSTEM AND METHOD FOR LOGGING ISOTOPE FRACTIONATION EFFECTS DURING MUD GAS LOGGING

BACKGROUND

Well bores are drilled to locate and produce hydrocarbons from geologic formations. A down hole drilling tool with a bit at an end thereof is advanced into the geologic formation to form a well bore. As the drilling tool is advanced, a drilling mud is pumped through the drilling tool and out the drilling tool to cool the drilling tool and carry away cuttings. The drilling mud additionally forms a mud cake that lines the well bore.

Formation evaluation often requires that fluid from the formation be drawn into the down hole tool for testing and/or sampling. Various devices, such as probes, are extended from the down hole tool to establish fluid communication with the formation surrounding the well bore and to draw fluid into the down hole tool. A typical probe is a circular element extended from the down hole tool and positioned against the sidewall of the well bore. A rubber packer at the end of the probe is used to create a seal with the wall of the well bore. Another device used to form a seal with the well bore is referred to as a dual packer. With a dual packer, two elastomeric rings expand radially about the tool to isolate a portion of the well bore there between. The rings form a seal with the well bore wall and permit fluid to be drawn into the isolated portion of the well bore and into an inlet in the down hole tool.

The mud cake lining the well bore is often useful in assisting the probe and/or dual packers in making the seal with the well bore wall. Once the seal is made, fluid from the formation is drawn into the down hole tool through an inlet by lowering the pressure in the down hole tool. Examples of probes and/or packers used in down hole tools are described in U.S. Pat. Nos. 6,301,959; 4,860,581; 4,936,139; 6,585,045; 6,609,568 and 6,719,049 and U.S. Patent Application No. 2004/0000433.

Formation evaluation is typically performed on fluids drawn into the down hole tool. Techniques currently exist for performing various measurements, pretests and/or sample collection of fluids that enter the down hole tool.

Fluid passing through the down hole tool may be tested to determine various down hole parameters or properties. The thermophysical properties of hydrocarbon reservoir fluids, such as viscosity, density and phase behavior of the fluid at reservoir conditions, may be used to evaluate potential reserves, determine flow in porous media and design completion, separation, treating, and metering systems, among others.

Formation evaluation may also be performed on gasses entering the drilling mud. One technique for performing this evaluation is known in the art as gas phase chromatography. Gas phase chromatography is a technique which may be used for the separation and quantification of mud gas components. Mud gas analysis using gas phase chromatography may allow monitoring of the drilling process for safety and performing a pre-evaluation of the type of fluids encountered in drilled formations. To extract gases from the drilling fluid, a gas extractor (often called degasser) such as the Geoservices Extractor, U.S. Pat. No. 7,032,444 may be used. Alternatively, selective membranes and sonication, have been used to release gas from the drilling fluid. After extraction, the mud gases may be transported and analyzed directly in a mud logging unit. It may be desirable to perform a qualitative and/or quantitative continuous compositional or isotopic analysis on fluids involved in mud gas analysis to be able to characterize the hydrocarbons present in the drilled formations versus depth. The more measurements performed, the better the level of resolution of gas events described by the mud logging services.

In the past few years, continuous real time (CRT) logging of isotopic compositions (typically expressed as delta—$\delta$, e.g. $\delta^{13}C$) of methane extracted from drilling mud during drilling operation was introduced as an additional tool for real time geochemical interpretations of the hydrocarbon system (Jones et al. 2005, Breviere et al. 2008, Breviere et al. 2009). Isotopic composition of methane (i.e. $\delta^{13}C$ or $\delta^2H$ also written as $\delta D$) as well as other gases have been used for several decades now for such interpretations, e.g. Bernard et al. 1978, Schoell 1983, Berner & Faber 1988, Whiticar 1999, etc.). Real time isotope logging as well as spot sampling (e.g. Isotubes) introduce many challenges for obtaining isotopic composition of gases representative of the formation gas or results of PVT-sample quality (results comparable to fluid samples taken from reservoir at reservoir pressure and temperature conditions). Main challenges include contamination by hydrocarbons generated via bit metamorphism (Faber et al. 1988, Wenger et al. 2009) and by gases recycled in mud during drilling operation. Whether isotopically unchanged or fractionated by surface degassing, the recycled gas will mix with formation gas and to certain extent affect the composition of the measured gas that is coming out with the mud.

The recycling issue for molecular gas composition has been addressed by quantitatively analyzing mud gas coming out (gas OUT) of bore hole and gas from mud that is being injected. Synchronization of these gases and subtraction of the gas going into the borehole (gas IN) provides quantitative formation gas composition of methane, ethane, propane, iso-butane, n-butane, iso-pentane, and n-pentane, i.e. in Fluid Logging and Analysis in Real-time (FLAIR) technology (Duriez et al. 2002, Breviere and Evrard 2006, Frechin and Breviere 2006, McKinney et al 2007). Currently there is no correction to account for recycling being applied in isotope logging.

Mud degassing, in general, will preferentially leave heavier gas species (e.g. $^{13}C$-enriched) retained in the mud to the degree controlled by i) $\alpha$ and ii) fraction of gas species not-degassed. The less gas remaining in the mud the more $^{13}C$-enriched the gas will be according to the kinetic isotopic fractionation $\alpha$ (in this case it is an open system, where liberated gas is removed from the system as it escapes to the atmosphere). Conversely, mud gas fraction extracted for analysis in a mud gas extractor will likely by slightly $^{13}C$-depleted, as such extraction is never complete and the liberated gas will be $^{12}C$-enriched. The degree of gas retention and recycling in mud as well as the isotopic fractionation during mud degassing can vary with mud and atmospheric conditions (e.g. temperature), time each portion of mud spends at the surface conditions exposed to atmosphere, type of mud (e.g. water based mud or oil based mud), type of additives (e.g. with sorption affinity for hydrocarbon gases, such as lignite), mud salinity, mud density, intensity of mud agitation and/or centrifuging on the surface, type of shale shakers, etc. Correction for extraction efficiency coefficient (EEC) for gaseous hydrocarbons has been successfully applied by using isobaric and isothermal conditions in a constant volume-degasser (Frechin and Breviere 2006).

Recently, continuous real-time isotope logging has been used to obtain $\delta^{13}C$ measurements from the mud gas that is being extracted from mud continuously flowing out of the wellbore during drilling. (See Jones et al. 2005, Breviere et al. 2008, Breviere et al. 2009). A development of applying Cavity Ring Down Spectroscopy to $\delta^{13}C1$ analysis was introduced a few years earlier (Uehara et al. 2001). This measurement provides isotopic composition of a mixture of freshly drilled formation gas, recycled gas, and bit-metamorphism gases (Faber et al. 1988, Wenger et al. 2009), and in specific conditions (e.g. underbalanced mud weight) intrusions of gas from already drilled shallower formations.

However, the readings obtained by the conventional techniques suffer from many drawbacks including inaccuracy of reading the isotopic composition of gas due to the impact of mixing formation gas with gas recycled in the drilling mud.

SUMMARY

This summary is provided to introduce a selection of concepts that are further described in the detailed description. This summary is not intended to identify key or essential features of the claimed subject matter, nor is it intended to be used as an aid in limiting the scope of the claimed subject matter.

In general, the present disclosure is directed to techniques to generate isotopic compositions of formation gas entering drilling mud from a geologic formation during a well drilling operation in which drilling mud is recirculated through the well-bore being formed by a drilling tool. The isotopic compositions of gas are preferably determined by equipment located outside of the well-bore.

It has been found that mud gas undergoes kinetic isotopic fractionation thereby and changing its isotopic composition during normal operational procedures during drilling, i.e. during degassing of mud at the surface in a mud pit and in a degasser, as well as during mixing of fractionated recycled gas remaining in the mud with gas originating from the freshly drilled formation. Therefore the isotopic composition of the mud gas species (e.g. methane, ethane, propane, iso-butane, butane, CO2, etc., as well as more than one element within one gas species, e.g. C and H isotopes in methane) of interest measured at the surface depends on (i) level of retention of a gas species in the mud (recycled gas fraction) and on (ii) isotopic fractionation associated with mud degassing on the surface, as well as (iii) on contribution of the recycled gas in relation to formation gas. The system and processes described herein, measures the isotopic compositions of formation gas and recycled gas within the drilling mud, and then determines the isotopic composition of the formation gas by correcting for isotopic compositions of the recycled gas.

In one version, the present disclosure describes a mud gas analyzer for analyzing drilling mud. The mud gas analyzer is provided with at least one degasser, at least one gas analyzer, and a computer system. The degasser is adapted to extract gas from drilling mud passing through a flow path formed at least partially by a drill string within a well and an annulus positioned between an exterior surface of the drill string and a formation surrounding the well at a well-site. In one embodiment, two degassers (for mud IN and mud OUT) are required to maintain constant mud flow and temperature, and to assure direct quantitative comparison of gas IN and gas OUT. Subsequently, extracted gas may travel towards the analyzer via a gas line, for example. Constant gas flow within the gas line may be assured by a gas flow restrictor. However, a gas analyzer might be instead placed directly at the degasser. The gas analyzer interacts with the mud gas passing through the flow path and generates a sequence of signals indicative of the gas molecular compositions (methane, ethane, propane, etc.) and ratios of isotopes of a gas species (e.g. $^{13}C/^{12}C$ of methane) within the drilling mud. The computer system includes a processor adapted to execute logic to cause the processor to receive the sequence of signals and calculate and log isotopic characteristics of formation gas entering the drilling mud at particular locations of the well (i.e. X, Y, Z, e.g. latitude, longitude, TVD). Logging isotopic characteristics of formation gas may be accomplished by accessing information indicative of a geometry of the well, a tool string positioned within the well, and optionally other components of the well site, including mud flow pumps, and the like, i) receive the sequence of signals, and ii) calculate and log. Such calculations may include synchronization of gas IN and OUT at the drilling bit, depth projection of time-synchronized data, gas molecular composition, isotopic ratios and any corrections (e.g. for extraction efficiency, contamination or recycling) to finally arrive at gas molecular and isotopic compositions of the formation gas.

In another embodiment, the present disclosure describes a well-site system including a drill string, a container for containing drilling mud, a mud pump, at least one degasser, at least one gas analyzer, and a computer system. The drill string includes a drilling tool positioned in a formation to bore a well through the formation thereby creating an annulus between an exterior surface of the drill string and the formation. The well has an entrance created by the initial boring of the well. A container containing drilling mud is fluidly connected to the entrance of the well to receive drilling mud from the well. The mud pump includes an inlet receiving the drilling mud from the container, and an outlet injecting drilling mud into the drill string through a flow path formed at least partially by the drill string and the annulus. The degasser is adapted to extract gas from drilling mud passing through a flow path formed at least partially by the drill string within the well and the annulus. In one embodiment, two degassers (for mud IN and mud OUT) are required to maintain constant volume, mud flow and temperature (including constant, and same temperatures of the degassers), and to assure direct quantitative comparison of gas IN and gas OUT. Subsequently, extracted gas may travel towards the analyzer via a gas line, for example. Constant gas flow within the gas line may be assured by a regulator such as a micrometric valve, a restrictor or any other gas flow regulating device. However, a gas analyzer might be instead placed directly at the degasser. The gas analyzer interacts with the mud gas passing through the flow path and generates a sequence of signals indicative of the gas molecular compositions (methane, ethane, propane, etc.) and ratios of isotopes of a gas species (e.g. $^{13}C/^{12}C$ of methane) within the drilling mud. The at least one gas analyzer is adapted to interact with the gas passing through the flow path, and to generate a sequence of signals indicative of ratios of isotopes of a species of gas extracted from the drilling mud. The computer system includes a processor adapted to execute logic to cause the processor to calculate and log the isotopic characteristics of gas entering the drilling mud at particular locations of the well. Calculating and logging isotopic characteristics can be accomplished by accessing information indicative of the geometry of the well and the tool string within the well.

In another embodiment, the present disclosure describes a computer system including one or more non-transitory computer readable medium storing processor executable code. The processor executable code is processed by the one or more processors of the computer system. The processor receives information indicative of the geometry of the well, and the geometry of the tool string from one or more communication devices and/or input devices of the computer system. The processor receives a sequence of signals indicative of ratios of isotopes of gas species of gas extracted from drilling mud from the one or more communication devices and/or input devices of the computer system. The processor receives a signal indicative of a flow rate of the drilling mud passing through the flow path from the one or more communication devices, and/or input devices of the computer system. The computer system then processes and calculates and logs isotopic characteristics of gas entering the drilling mud at particular locations of the well (referred to as formation gas) using the information indicative of the geometry of the well, geometry of the tool string, the flow rate of the drilling mud, and the signals indicative of ratios of isotopes of the gas species.

BRIEF DESCRIPTION OF DRAWINGS

Certain embodiments of the present inventive concepts will hereafter be described with reference to the accompanying drawings, wherein like reference numerals denote like elements, and.

DESCRIPTION OF EXEMPLARY EMBODIMENTS

Specific embodiments of the present disclosure will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Figure 1:
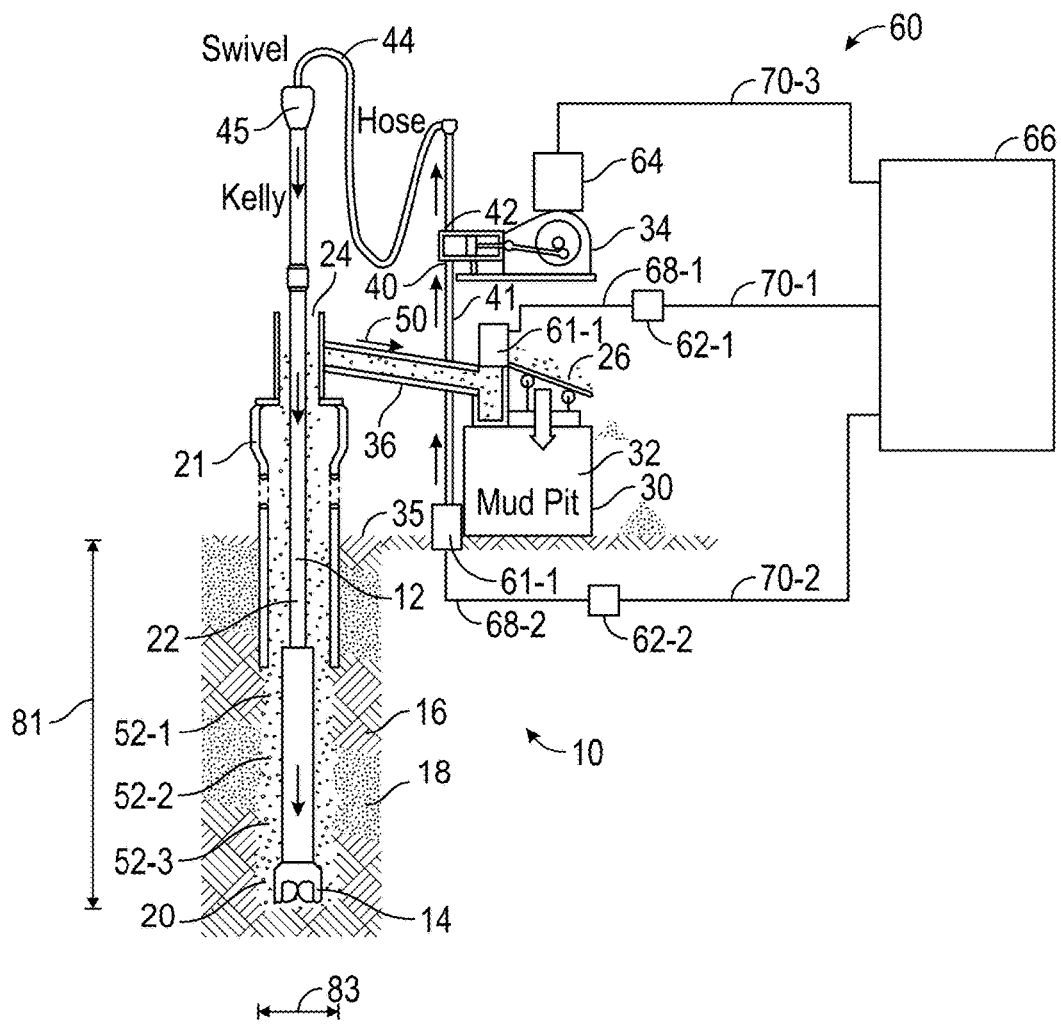
FIG. 1 is a schematic view of one embodiment of a well-site system constructed in accordance with the present disclosure for logging isotopic compositions of gas coming from a geologic formation during continuous real-time mud gas logging.

Referring now to the drawings and in particular to FIG. 1, shown therein and designated by a reference numeral 10 is a wellsite system constructed in accordance with the present disclosure. The wellsite system 10 is provided with a drill string 12 connected to a drilling tool 14 being advanced through a geologic formation 16 to form a wellbore 18. The drilling tool 14 can be conveyed among one or more (or itself may be) a measurement-while-drilling (MWD) drilling tool, a logging-while-drilling (LWD) drilling tool, or other drilling tool that are known to those skilled in the art. The drilling tool 14 is attached to the drill string 12 and is driven by a rig (not shown) to form the wellbore 18 thereby creating an annulus 20 between an exterior surface 22 of the drill string 12 and the geologic formation 16. The wellbore 18 may be lined with a casing 21 provided with an entrance 24 through which the drill string 12 passes.

The wellsite system 10 is also provided with one or more shale shaker 26, positioned adjacent to one or more container 30 containing drilling mud 32. The wellsite system 10 is also provided with one or more mud pump 34 circulating the drilling mud 32 through the drill string 12, the drilling tool 14 and the annulus 20 while the drilling tool 14 is being advanced into the geologic formation 16. As discussed above, the drilling mud 32 serves a variety of functions including, but not limited to, lubricating the drilling tool 14 and conveying the cuttings to a surface 35 of the geologic formation 16. The container 30 is connected to the entrance 24 of the wellbore 18 via a first flow line 36.

The shale shaker 26 is known in the art and can be implemented in a variety of manners. In general, the shale shaker 26 serves to remove cuttings from the drilling mud 32. In one embodiment, the shale shaker 26 may include a vibrating screen with openings through which the drilling mud 32, but not the cuttings, may pass.

After passing through the shale shaker 26, the drilling mud 32 passes into the container 30. The container 30 can be constructed in a variety of forms and may be a structure referred to in the art as a "mud pit."

The mud pump 34 has an inlet 40 receiving drilling mud 32 from the container 30 via a second flow line 41, and an outlet 42 injecting drilling mud into the drill string 12 through a mud injection line 44. In the example shown in FIG. 1, the mud injection line 44 is connected to the drill string 12 via a swivel 45 to permit the drill string 12 to be rotated via a kelly (not shown) relative to the mud injection line 44 thereby aiding the drilling tool 14 in forming the wellbore 18. The mud pump 34 circulates drilling mud 32 through a flow path 50 (shown by way of arrows in FIG. 1) formed sequentially by the mud injection line 44, an inner bore (not shown) of the swivel 45, an inner bore (not shown) of the drill string 12, an inner bore (not shown) of the drilling tool 14, the annulus 20 of the wellbore 18, the first flow line 36, the container 30 and the second flow line 41.

As will be explained in more detail below, the drilling mud 32 received from the annulus 20 contains a mixture of gases received from the geologic formation 16, and residual gases (also known as "recycled gas") that were entrained in the drilling mud 32 prior to injection into the drill string 12 via the mud pump 34. The drilling mud 32 undergoes a process known in the art as "mud degassing" while the drilling mud 32 is passing through the shale shaker 26 and the container 30 in which gases entrained in the drilling mud 32 are liberated into the surrounding atmosphere. For example, lighter isotopes, i.e. $^{12}C$ vs heavier isotopes $^{13}C$ are preferentially liberated during mud degassing at the surface 35 causing the gases within the drilling mud 32 to undergo a process known in the art as "isotopic fractionation". In general, the drilling mud 32 that is injected into the drill string 12 after "mud degassing" and "isotopic fractionation" is enriched in heavier isotope gases (e.g. enriched in $^{13}CH_4$) relative to lighter isotope gases. Even assuming that that isotope fractionation of the gas during "mud degassing" is not taking place, formation gas entering the drilling mud 32 may be different from the recycled gas entrained in the drilling mud 32 since new parts of the formation 16 are being exposed during the drilling process.

To determine isotopic characteristics of gas entering the drilling mud 32 at particular locations 52-1, 52-2, 52-3 (and the like) of the wellbore 18, the wellsite system 10 is provided with a mud gas analyzer 60 constructed in accordance with the present disclosure. The mud gas analyzer 60 may be entirely provided above the surface 35 of the geologic formation 16. Thus, in this example, the mud gas analyzer 60 would not include any components which are located below the surface 35 of the geologic formation 16.

In one embodiment, the mud gas analyzer 60 is provided with at least one gas extractor (degasser) 61, at least one gas analyzer 62, an optional at least one flowmeter 64, and a computer system 66. In the example depicted in FIG. 1, the mud gas analyzer 60 is provided with two degassers 61-1 and 61-2, two gas analyzers 62-1 and 62-2 with the gas analyzer 62-1 being positioned adjacent to and/or within the first flow line 36 between the entrance 24 and the shale shaker 26, and the gas analyzer 62-2 being positioned adjacent to and/or within the second flow line 41 and/or the mud injection line 44. The degasser 61-1 extracts gas from the drilling mud 32 and directs the gas to the gas analyzer 62-1 via a third flow line 68-1. The degasser 61-2 extracts gas from the drilling mud and directs the gas analyzer 62-2 via a fourth flow line 68-2. The at least one degasser 61 can be implemented as any device adapted to extract gas from the drilling mud 32 and direct the gas to the at least one mud gas analyzer 60. For example, the at least one degasser 61 can be implemented in a manner taught in U.S. Pat. No. 7,032,444. In other embodiments, other types of devices and/or processes can be used such as selective membranes and sonication, to release gas from the drilling fluid.

In one embodiment, two degassers 61-1 and 61-2 (for mud IN and mud OUT) are required to maintain constant mud flow and temperature (including constant, and same temperatures of the degassers), and to assure direct quantitative comparison of gas IN and gas OUT. Subsequently, extracted gas may travel towards the analyzers 62-1 and 62-2 via the third and fourth flow lines 68-1 and 68-2 gas line, for example. Constant gas flow within the third and fourth flow lines 68-1 and 68-2 may be assured by a gas flow restrictor. However, the gas analyzers 62-1 and 62-2 might be instead placed directly at the degassers 61-1 and 61-2. The gas analyzers 62-1 and 62-2 interacts with the mud gas passing through the third and fourth flow lines 68-1 and 68-2 and generate a sequence of signals indicative of the gas molecular compositions (methane, ethane, propane, etc.) and ratios of isotopes of a gas species (e.g. $^{13}C/^{12}C$ of methane) within the drilling mud.

The mud gas analyzer 60 is also provided with a first communication link 70-1 connecting the gas analyzer 62-1 to the computer system 66, a second communication link 70-2 connecting the gas analyzer 62-2 to the computer system 66, and a third communication link 70-3 connecting the flowmeter 64 to the computer system 66. The first, second and third communication links 70-1, 70-2, and 70-3 may be implemented via wired or wireless devices, such as a cable or a wireless transceiver. In general, the first and second communication links 70-1 and 70-2 establish electrical and/or optical communications between the gas analyzers 62-1 and 62-2 and the computer system 66; and the third communication link 70-3 establishes electrical and/or optical communications between the flowmeter 64 and the computer system 66. In one embodiment, the gas analyzer 62-1, the gas analyzer 62-2, the flowmeter 64, the computer system 66, the first communication link 70-1, the second communication link 70-2 and the third communication link 70-3 are located above the surface 35 of the geologic formation 16.

The gas analyzer 62-1 and/or the gas analyzer 62-2 are adapted to interact with the drilling mud 32 as the drilling mud 32 passes through the flow path 50 formed at least partially by the drill string 12 within the wellbore 18 and the annulus 20. In the example depicted in FIG. 1, the gas analyzer 62-1 interacts with the drilling mud 32 passing from the entrance 24 to the shale shaker 26 which drilling mud 32 will be referred to herein as drilling mud OUT. The drilling mud OUT contains non-liberated residual gas that is enriched in heavier isotopes. In this example, the gas analyzer 62-2 interacts with the gas from the drilling mud 32 passing from the container 30 to the drill string 12 which drilling mud 32 will be referred to herein as drilling mud IN. The drilling mud IN has been subject to mud degassing as well as isotopic fractionation and thus has an isotopic composition that is different from the drilling mud OUT.

The at least one gas analyzer 62, such as the gas analyzer 62-1 and/or the gas analyzer 62-2 can be implemented with any type of device and/or circuitry (or devices working together) adapted to determine and generate a sequence of first signals indicative of ratios of isotopes of one or more molecules of gas within the drilling mud 32 at separate (and/or distinct) instants of time. For example, any type of gas analyzing device that can measure isotopic concentrations to obtain a ratio of the isotopic measurements can be used. For example, the at least one gas analyzer 62 can be implemented as gas chromatograph-isotope ratio mass spectrometer (GC-IRMS), and/or a spectrophotometer or photoacoustic detector working on the TDLAS (Tunable Diode Laser Absorption Spectroscopy) principle or the CRDS 5 Cavity Ring Down Spectroscopy) or any other technology able to provide relative concentration of isotopes of a gas species (e.g. $^{13}C$ and $^{12}C$ in $CH_4$ or $^{18}O$ and $^{16}O$ in $CO_2$, etc.). Further, although two gas analyzers 62-1 and 62-2 are shown and described herein, in other embodiments, the mud gas analyzer 60 may include one gas analyzer 62, or more than two gas analyzers 62. For example, in various embodiments, the mud gas analyzer 60 may include 1, 2, 3, 4, 5, 6, 7, 8, etc. gas analyzers 62. Additionally, the mud gas analyzer 60 may include one of the gas analyzers 62 being used to emulate two or more gas analyzers 62 by using a valve in combination with the gas analyzer 62 to direct more than one flow line to the gas analyzer 62.

The at least one flowmeter 64 includes suitable devices and/or circuitry to determine a rate of flow of the drilling mud 32 and to generate a sequence of signals as the drilling mud 32 is circulated through the flow path 50 at separate and/or distinct instants of time. As will be discussed below, the sequence of signals, and/or a known flow rate of the drilling mud can be utilized by the computer system 66 to determine a delay time that can be used to synchronize the reading of the drilling mud IN with the reading of the drilling mud OUT and perform the depth projection, so that the isotopic characteristics of the geologic formation 16 can be determined. In one embodiment, the flowmeter 64 is implemented as a device that determines the flow rate indirectly by counting rotations of a spindle of the mud pump 34 when the mud pump 34 pumps a known amount of drilling mud 32 with each rotation. However, it should be understood that the flowmeter 64 can be implemented in other manners. For example, the flowmeter 64 can be implemented in a manner to apply a medium, such as magnetic flux lines, into the drilling mud 32 to directly measure the flow rate of the drilling mud 32. In this instance, the flowmeter 64 would have a transmitter/receiver pair to generate the medium, and receive the medium after the medium has interacted with the drilling mud 32. Further, in various embodiments, the mud gas analyzer 60 may include 1, 2, 3, 4, 5, 6, 7, 8, etc. flowmeters 64. The sequence of signals can be provided in electrical and/or optical formats, for example.

Figure 7:
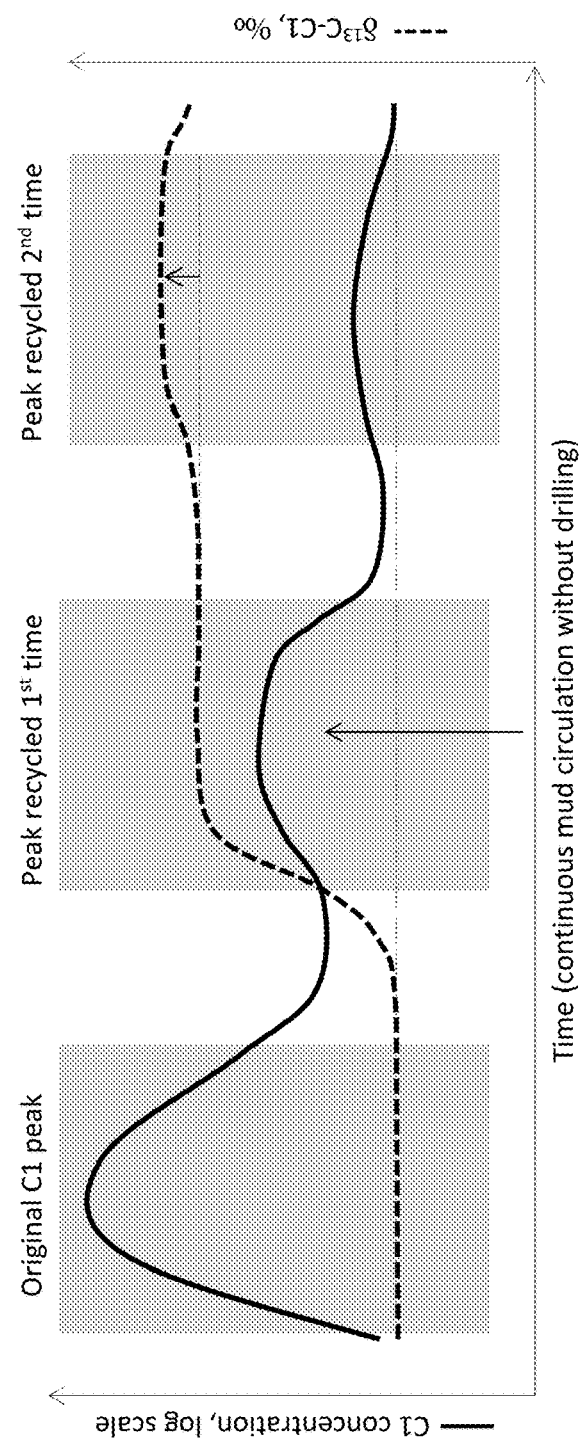
FIG. 7 is a graph showing field observations of isotope fractionation of recycled C1, where the sold line shows observed C1 concentrations, and the dashed line shows observations of isotopic compositions values.
Figure 11:
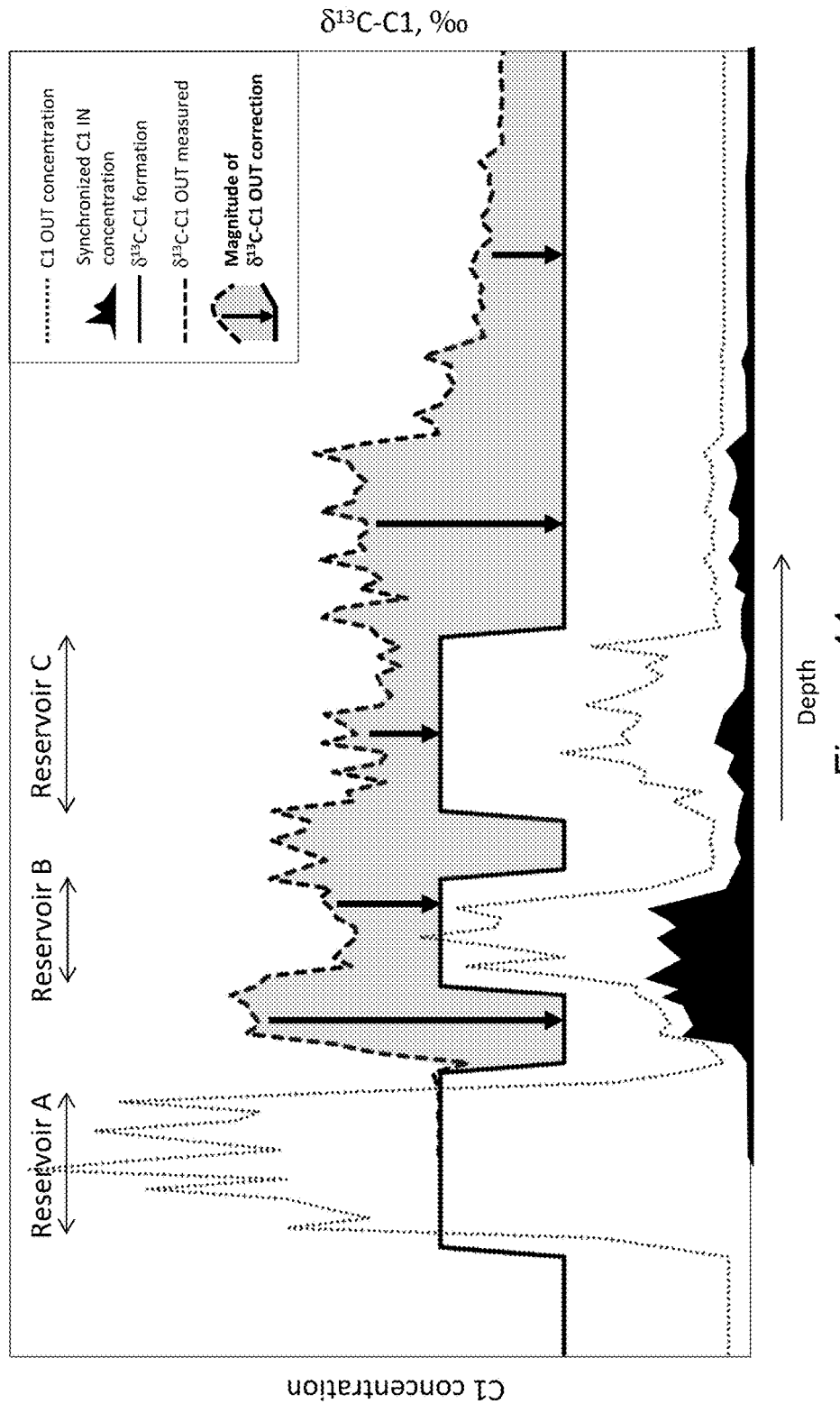
FIG. 11 is an exemplary calculated log of isotopic characteristics of a gas species entering the drilling mud at particular locations of the well using information indicative of a flow of the drilling mud, the geometry of the well and the geometry of the tool string or using information from any other source providing particular locations of the well at which mixing of fractions of a gas species occurred. This exemplary model log for methane (C1) shows the extent of discrepancy (highlighted as grey area) of $\delta^{13}C\text{-}C1_{OUT}$ measured (dashed line) at the surface without correction described herein and the correct $\delta^{13}C\text{-}C1_{formation}$ (solid line).

This disclosure describes the process of isotopic fractionation during recycling of fractions of mud gas during a drilling operation and proposes analytical and mathematical correction methods of the measured $\delta_{OUT}$ values to represent the formation gas isotopic composition ($\delta_{formation}$) The disclosure also describes this process by using a sensitivity model to create a log of isotopic characteristics of gas. An exemplary log is shown in FIG. 11, in which calculated values for the formation gas is shown as a solid line, and a gray area is shown as a correction for each depth of the wellbore 18. In the example shown in FIG. 11, the wellbore 18 intersects three reservoirs, i.e., Reservoir A, Reservoir B and Reservoir C containing the same fluid. The log shown in FIG. 11 also shows an extent of error in $\delta^{13}C$-C1 caused by isotope recycling in Reservoirs B and C and in the background intervals. Uncorrected $\delta^{13}C$-C1 OUT measured implies three compartments with three different $\delta^{13}C$-C1, where in reality all have the same $\delta^{13}C$-C1 Formation. The δ notation is an globally recognized expression of a heavy/light isotope ratio scaled to an international standard, i.e. in case of stable carbon (C) isotope ratio the definition is $\delta^{13}C=[(^{13}C/^{12}C)_{sample}/(^{13}C/^{12}C)_{international\ standard})-1]*1000$, the unit is ‰, C1 stands for methane (an alkane with one C atom), and the international standard for carbon isotopes is V-PDB which has an $^{13}C/^{12}C$ ratio of the absolute accepted value equal to 0.0112372. FIG. 7 shows field observations of isotope fractionation during surface degassing of mud of recycled C1 peak, where the solid line shows C1 concentration, and the dashed line shows isotopic composition.

The model shows extent of impact of the isotope recycling on the $\delta_{OUT}$. The factors controlling the impact are (i) fraction of not degassed gas species on the surface (residual fraction–$f_{residual}$), (ii) isotopic fractionation factor of the mud degassing process on the surface $\alpha_{surface}$, (iii) relative contribution of gas species IN to OUT synchronized at bit ($f_{IN}$, where $f_{formation}=1-f_{IN}$), and finally (iv) the difference between $\delta_{formation}$ and $\delta_{IN}$ ($\Delta_{formation-IN}=\delta_{formation}-\delta_{IN}$). $\delta_{IN}$ represents the residual fraction or not degassed fraction of gas species, that gets re-injected as gas species IN.

Note, that even with $\alpha_{surface}=1$ (no isotopic fractionation during mud degassing at the surface), the impact of isotope recycling might still be present, and its magnitude will be proportional to the $f_{formation}$ and $\Delta_{formation-IN}$. The largest impact on the $\delta_{OUT}$ will be when the $\Delta_{formation-IN}$ and the IN/OUT ratio of a gas species are the largest. Large $\Delta_{formation-IN}$ can be a combination of either or both (i) high intrinsic variability of subsequently underlying formation gases, and (ii) large $\alpha_{surface}$. Conversely, if coincidentally $\delta_{IN}=\delta_{formation}$ of underlying formation then the impact of isotope recycling will be diminished. Relative contribution of gas species IN to OUT synchronized at bit depends on i) level of recycling of a mud gas species and ii) relative differences in C1 coming from subsequent formations.

To perform the analytical and mathematical correction methods of the measured $\delta_{OUT}$ values to represent the formation gas isotopic composition ($\delta_{formation}$), the computer system 66 includes a processor 80 (shown in FIG. 2) that is adapted to execute logic to cause the processor 80 to access information indicative of a geometry of the wellbore 18 and a tool string that includes the drill string (12) and the drilling tool (14), receive the sequence of signals, and to calculate and log isotopic characteristics of gas entering the drilling mud 32 at particular locations (e.g., location 52-1, location 52-2, and location 52-3) of the geologic formation 16. The geometry of the wellbore 18 may include a variety of factors, such as a length 81 of the wellbore 18, a diameter 83 of the wellbore 18 and geometry/volumetrics of the tool string. The geometry of the tool string includes diameter and combined length of the drill string 12 and the drilling tool 14 as well as depth of the bit and structural configuration of the drilling tool 14 (e.g., including all elements of the entire bottom hole assembly). Information regarding the geometry of the wellbore 18, and the geometry of the tool string can be entered into the computer system 66 by an operator when a change to the tool string is being made, for example. The locations 52-1, 52-2 and 52-3 of the geologic formation 16 may be described using any suitable geographic coordinate system including at least one number representing vertical position, and two or three numbers representing horizontal position. For example, a suitable geographic coordinate system uses latitude, and longitude to identify horizontal position, and elevation to identify vertical position.

The logic may be adapted to correct for isotope recycling, via synchronization of readings of drilling mud IN and drilling mud OUT isotopic and quantitative concentration data and by applying a mass balance equation, such as:

$\delta_{formation}=(\delta_{OUT}-f_{IN}*\delta_{IN})/f_{formation}$. This calculation is an approximation of actual material balance. However, error introduced by this calculation to $\delta_{formation}$ is at worst one order of magnitude smaller than the top-quality laboratory-precision of $\delta^{13}C$ measurement on gaseous n-alkanes (0.1‰). Nonetheless, a more accurate calculation of $\delta_{formation}$ can be obtained by the following equation:

$$\delta_{formation} = 1000\left(\frac{\frac{R_{OUT}/R_{STD}}{1+R_{OUT}} - \frac{f_{IN}R_{IN}/R_{STD}}{1+R_{IN}}}{\frac{1}{1+R_{OUT}} - \frac{f_{IN}}{1+R_{IN}}} - 1\right)$$

where $f_{IN}$—fraction of drilling mud gas OUT that is not coming from formation, but is a portion of not degassed on the surface gas (or recycled gas), and:

$f_{formation}=1-f_{IN}$, and in case of methane (C1) $f_{IN}=C1_{IN}/C1_{OUT}$, where $C1=^{12}C+^{13}C$, and $R=^{13}C/^{12}C$ (e.g. $R_{STD}=^{13}C/^{12}C$ ratio of the absolute value of the international standard for carbon isotopes V-PDB equal to 0.0112372).

Especially, when there is likely isotopic fractionation associated with mud degassing on the surface 35, the injected not-degassed recycled gas cannot be assumed to have identical isotopic composition as the originally analyzed drilling mud gas OUT, prior to surface degassing.

To properly address the problem of isotopic recycling, various factors can be analyzed including (i) the level of retention of a gas species in the drilling mud 32 before the drilling mud 32 gets re-injected into the wellbore 18, and (ii) range of kinetic isotopic fractionation factor ($\alpha$). Finally, the isotopic composition of the formation gas ($\delta_{formation}$) will be a result of mass balance calculation of analyzed drilling mud gas IN and drilling mud gas OUT mixture, preferably synchronized at the elevation of the drilling tool 14 (so that both gas portions get assigned back to the same drilled depth and location). Such calculation can be applied to each gas species for which isotopic composition is being analyzed, owing to variable level of retention (recycling) and isotopic fractionation for individual gas species. As discussed above, correction for extraction efficiency for gaseous hydrocarbons has been successfully applied by using isobaric and isothermal conditions in a constant volume-degasser (Frechin and Breviere 2006). A similar framework of thermodynamically-controlled drilling mud gas IN and drilling mud gas OUT degassers might facilitate more accurate correction of the isotopic composition of mud gas. Alternatively to using two gas analyzers 62-1 and 62-2 for drilling mud gas OUT and drilling mud gas IN correction for isotopic composition of formation gas, an empirical method and the gas analyzer 62-1 for measuring only drilling mud gas OUT can be used, where rate of degassing and $\alpha_{surface}$ and degassing rate of the gas species $k_{surface}$ will be measured on-site prior to drilling and their dependence on parameters (mud type, temperature, etc.) may be experimentally established as well. This method will require continuous measurement of these parameters as well as of $t_{surface}$ (i.e., time on the surface) of each hypothetical batch of drilling mud, between the locations of the gas analyzers 62-1 and 62-2 for measuring the drilling mud gas OUT and drilling mud gas N. This latter method may pose more challenges and risks of errors than the direct method using two or more gas analyzers 62-1 and 62-2 measuring isotopic analyses of drilling mud gas IN and drilling mud gas OUT.

Figure 2:
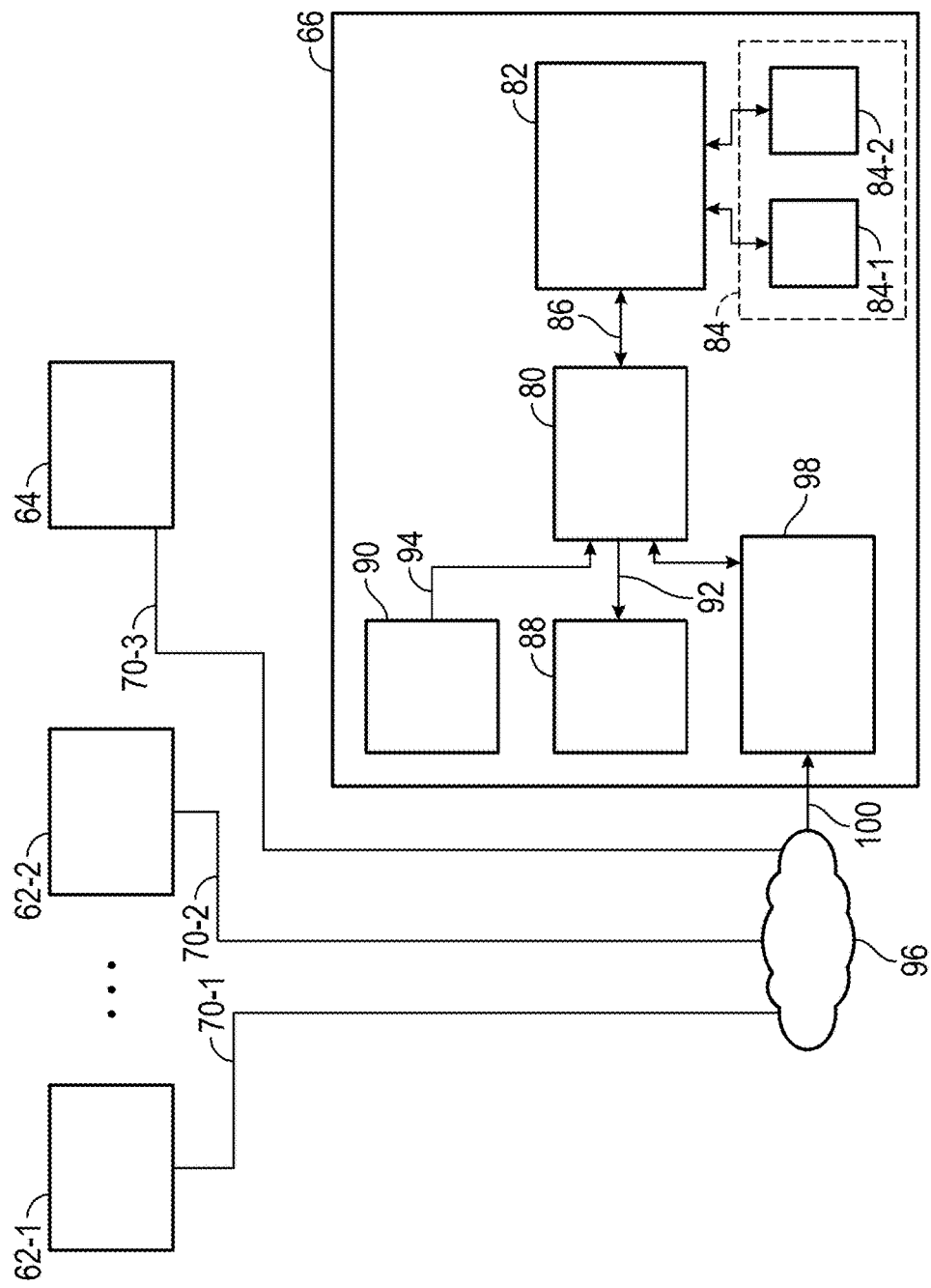
FIG. 2 is a schematic view of one embodiment of a mud gas analyzer constructed in accordance with the present disclosure.

Referring now to FIG. 2, shown therein is one embodiment of the computer system 66 connected to the gas analyzers 62-1 and 62-2, as well as to the optional flowmeter 64 to analyze the isotopic composition of the formation gas. The computer system 66 may comprise the processor 80, a non-transitory computer readable medium 82, and processor executable instructions 84 stored on the non-transitory computer readable medium 82. In another embodiment, the computer system 66 can receive flow/depth information from an operator or a flow/depth providing service.

The processor 80 may be implemented as any suitable hardware capable of performing the calculations and assisting to generate the logs described herein. For example, the processor 80 may include a single processor or multiple processors working together or independently to execute the processor executable instructions 84 described herein. Embodiments of the processor 80 may include a digital signal processor (DSP), a central processing unit (CPU), a microprocessor, a multi-core processor, an application specific integrated circuit, and combinations thereof. The processor 80 is coupled to the non-transitory computer readable medium 82. The non-transitory computer readable medium 82 can be implemented as RAM, ROM, flash memory or the like, and may take the form of a magnetic device, optical device or the like. The non-transitory computer readable medium 82 can be a single non-transitory computer readable medium, or multiple non-transitory computer readable medium functioning logically together or independently.

The processor 80 is coupled to and configured to communicate with the non-transitory computer readable medium 82 via a path 86 which can be implemented as a data bus, for example. The processor 80 may be capable of communicating with an input device 88 and an output device 90 via paths 92 and 94, respectively. Paths 92 and 94 may be implemented similarly to, or differently from path 86. For example, paths 92 and 94 may have a same or different number of wires and may or may not include a multidrop topology, a daisy chain topology, or one or more switched hubs. The paths 86, 92 and 94 can be a serial topology, a parallel topology, a proprietary topology, or combination thereof. The processor 80 is further capable of interfacing and/or communicating with one or more network 96, via the communications device 98 and a communications link 100 such as by exchanging electronic, digital and/or optical signals via the communications device 98 using a network protocol such as TCP/IP. The communications device 98 may be a wireless modem, digital subscriber line modem, cable modem, network bridge, Ethernet switch, direct wired connection or any other suitable communications device capable of communicating between the processor 80 and the network 96.

It is to be understood that in certain embodiments using more than one processor 80, the processors 80 may be located remotely from one another, located in the same location, or comprising a unitary multicore processor (not shown). The processor 80 is capable of reading and/or executing the processor executable instructions 84 and/or creating, manipulating, altering, and storing computer data structures into the non-transitory computer readable medium 82.

The non-transitory computer readable medium 82 stores processor executable instructions 84 and may be implemented as random access memory (RAM), a hard drive, a hard drive array, a solid state drive, a flash drive, a memory card, a CD-ROM, a DVD-ROM, a BLU-RAY, a floppy disk, an optical drive, and combinations thereof. When more than one non-transitory computer readable medium 82 is used, one of the non-transitory computer readable mediums 82 may be located in the same physical location as the processor 80, and another one of the non-transitory computer readable mediums 82 may be located in a location remote from the processor 80. The physical location of the non-transitory computer readable mediums 82 may be varied and the non-transitory computer readable medium 82 may be implemented as a "cloud memory," i.e. non-transitory computer readable medium 82 which is partially or completely based on or accessed using the network 96. In one embodiment, the non-transitory computer readable medium 82 stores a database accessible by the computer system 66.

The input device 88 transmits data to the processor 80, and can be implemented as a keyboard, a mouse, a touchscreen, a camera, a cellular phone, a tablet, a smart phone, a PDA, a microphone, a network adapter, a camera, a scanner, and combinations thereof. The input device 88 may be located in the same location as the processor 80, or may be remotely located and/or partially or completely network-based. The input device 88 communicates with the processor 80 via path 92.

The output device 90 transmits information from the processor 80 to a user, such that the information can be perceived by the user. For example, the output device 90 may be implemented as a server, a computer monitor, a cell phone, a tablet, a speaker, a website, a PDA, a fax, a printer, a projector, a laptop monitor, and combinations thereof. The output device 90 communicates with the processor 80 via the path 94.

The network 96 may permit bi-directional communication of information and/or data between the processor 80 and the gas analyzers 62-1 and 62-2, as well as the flowmeter 64. The network 96 may interface with the processor 80 in a variety of ways, such as by optical and/or electronic interfaces, and may use a plurality of network topographies and protocols, such as Ethernet, TCP/IP, circuit switched paths, file transfer protocol, packet switched wide area networks, and combinations thereof. For example, the one or more network 96 may be implemented as the Internet, a LAN, a wide area network (WAN), a metropolitan network, a wireless network, a cellular network, a GSM-network, a CDMA network, a 3G network, a 4G network, a satellite network, a radio network, an optical network, a cable network, a public switched telephone network, an Ethernet network, and combinations thereof. The network 96 may use a variety of network protocols to permit bi-directional interface and communication of data and/or information between the processor 80 and the network 96.

In one embodiment, the processor 80, the non-transitory computer readable medium 82, the input device 88, the output device 90, and the communications device 98 may be implemented together as a smartphone, a PDA, a tablet device, such as an iPad, a netbook, a laptop computer, a desktop computer, or any other computing device.

The non-transitory computer readable medium 82 may store the processor executable instructions 84, which may comprise a gas analysis and logging program 84-1. The non-transitory computer readable medium 82 may also store other processor executable instructions 84-2 such as an operating system and application programs such as a word processor or spreadsheet program, for example. The processor executable instructions for the gas analysis and logging program 84-1 and the other processor executable instructions 84-2 may be written in any suitable programming language, such as C++, C#, or Java, for example.

The gas analysis and logging program 84-1 may have processor executable instructions which enable control of the gas analyzers 62-1 and 62-2, the mud pump 34, the flowmeter 64 and combinations thereof. The gas analysis and logging program 84-1 may have processor executable instructions for receiving the sequences of first and second signals from the gas analyzers 62-1 and 62-2, and the flowmeter 64. To control the mud gas analyzer 60, the gas analysis and logging program 84-1, may allow for manual control of reading of the gas analyzers 62-1 and/or 62-2, as well as setting the flow rate of the drilling mud 32, as measured by the flowmeter 64, for example. The gas analysis and logging program 84-1 may have processor executable instructions, for interpreting and/or outputting information received from the gas analyzers 62 and the flowmeter 64 to create user perceivable outputs, in the form of reports, waveforms, or display screens for example, (an example of which is shown in FIG. 11) to provide a user with the information indicative of the isotopic characteristics of the formation gas at the particular locations 52-1, 52-2 and 52-2.

Figure 3:
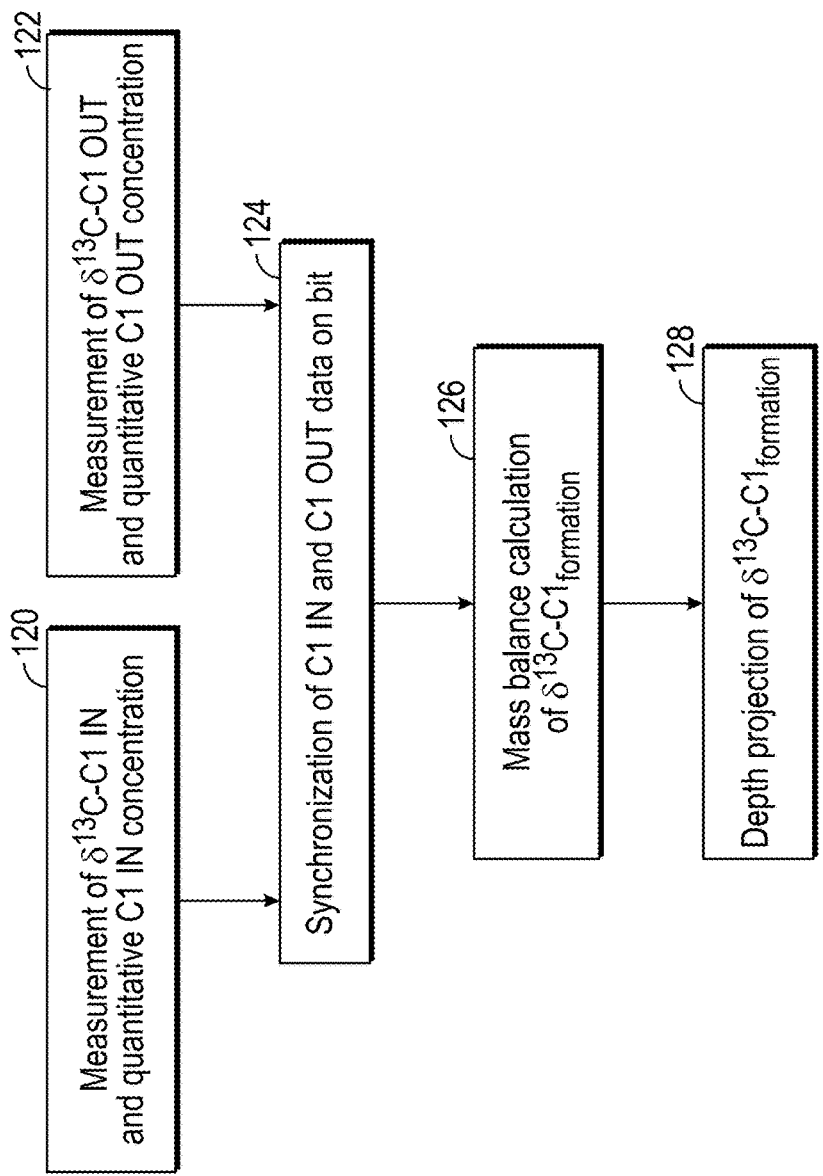
FIG. 3 is a logic flow diagram of one embodiment of gas analysis logic that causes a processor to calculate and log isotopic characteristics of gas entering the drilling mud at particular locations of the wellbore using a sequence of signals indicative of the ratios of isotopes of a species of gas within the drilling mud generated by at least two gas analyzers (or one gas analyzer emulating two gas analyzers) in accordance with the present disclosure.

Referring now to FIG. 3, shown therein is a diagrammatic representation of one embodiment of a method performed by the processor 80 of the mud gas analyzer 60 to measure the isotopic characteristics of the formation gas. The most straightforward and likely the most accurate correction of $\delta_{formation}$ values for recycling of mud gas can be achieved by utilizing gas concentration analysis using constant PVT mud degassing and isotopic analysis of drilling mud gas OUT and IN. In such scenario, a mass balance calculation of the $\delta_{formation}$ based on drilling tool-synchronized CRT measurements of gas fractions and their isotopic compositions can be used. In this case knowledge of $\alpha_{surface}$ is not necessary. On example of C1 the correction value that is applied to measured $\delta^{13}C$-$C1_{OUT}$ depends on: $\alpha^{13}C$-$C1_{surface}$, C1 IN/C1 OUT ratio, and relative difference between subsequently drilled formations, i.e. C1 concentration and $\delta^{13}C$-C1 of a gas from freshly drilled interval that mixes with gas not degassed from mud on the surface, that is a remnant of gas from overlying formation. However, the calculation for correction does not require knowledge of the $\alpha^{13}C$-$C1_{surface}$.

Although the mud gas analyzer 60 may be used to analyze qualitative and/or quantitative compositional and isotopic characteristics of fluids and gasses involved in mud gas analysis, for the sake of simplicity, the following description will recite the method in relation to the formation gas extracted from the drilling mud 32. The mud pump 34 is actuated to circulate the drilling mud 32 past the degassers 61-1 and 61-2 at a known flow rate, or flow rate monitored by the flowmeter 64 or kept constant by the design of the degasser for example. On an example of methane, a sequence of measurements of the isotopic characteristics of the drilling mud gas IN (e.g., $\delta^{13}C$-C1) and quantitative C1 IN concentration is taken by the gas analyzer 62-2, as shown in block 120. However, it should be understood that the mud gas analyzer 60 can be used for reading other isotopes, and other isotopic characteristics of other types of gases including methane, ethane, propane, iso-butane, butane, $CO_2$, etc., as well as more than one element within one gas species, e.g. C and H isotopes in methane. Similarly, a sequence of measurements of the isotopic characteristics of the drilling mud gas OUT (e.g., $\delta^{13}C$-C1) and quantitative C1 OUT concentrations is taken by the gas analyzer 62-1, as shown in block 122. The sequence of measurements of the C1 IN and C1 OUT data is synchronized on the bit (i.e., when the drilling mud 32 is located at the bottom of the wellbore 18) as shown in block 124 using data indicative of the geometry of the wellbore 18 the geometry of the tool string, as well as the flow rate of the drilling mud 32 to determine a time-based delay time and use the computation to synchronize gas IN and gas OUT and to calculate a depth at which this synchronization occurs. The isotopic characteristics of the formation gas on example of methane may then be calculated using a suitable mass balance equation in a block 126, such as:

$$\delta^{13}C\text{-}C1_{formation} = (\delta^{13}C\text{-}C1_{OUT} - f_{IN} * \delta^{13}C\text{-}C1_{IN})/(1-f_{IN}),$$

where $f_{IN}$ is fraction of $C1_{OUT}$ not coming from the formation and is the re-injected residual gas that did not degas from the mud on the surface. The fraction of C1 from the formation ($C1_{formation}$) within the $C1_{OUT}$ equals to $f_{formation} = 1 - f_{IN}$.

As shown by block 128, the isotopic characteristics of the formation gas are then associated with a particular location, such as 52-1, 52-2 and/or 52-3 within the wellbore 18 and/or geologic formation 16.

Figure 4:
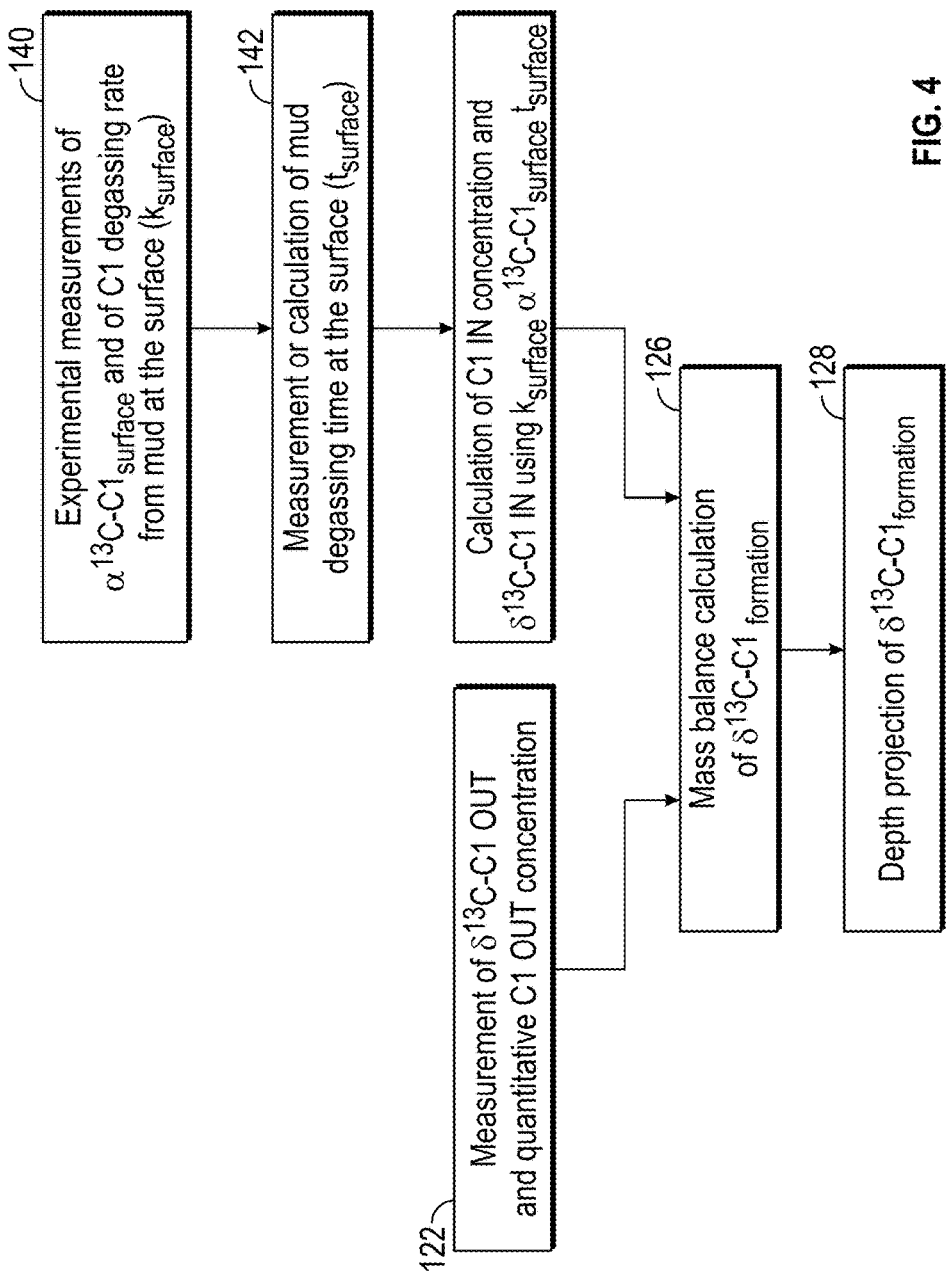
FIG. 4 is a logic flow diagram of another embodiment of gas analysis logic that causes a processor to calculate and log isotopic characteristics of gas entering the drilling mud at particular locations of the well using a sequence of signals indicative of the ratios of isotopes of a molecule of gas within the drilling mud generated by a gas analyzer in accordance with the present disclosure.
Figure 8:
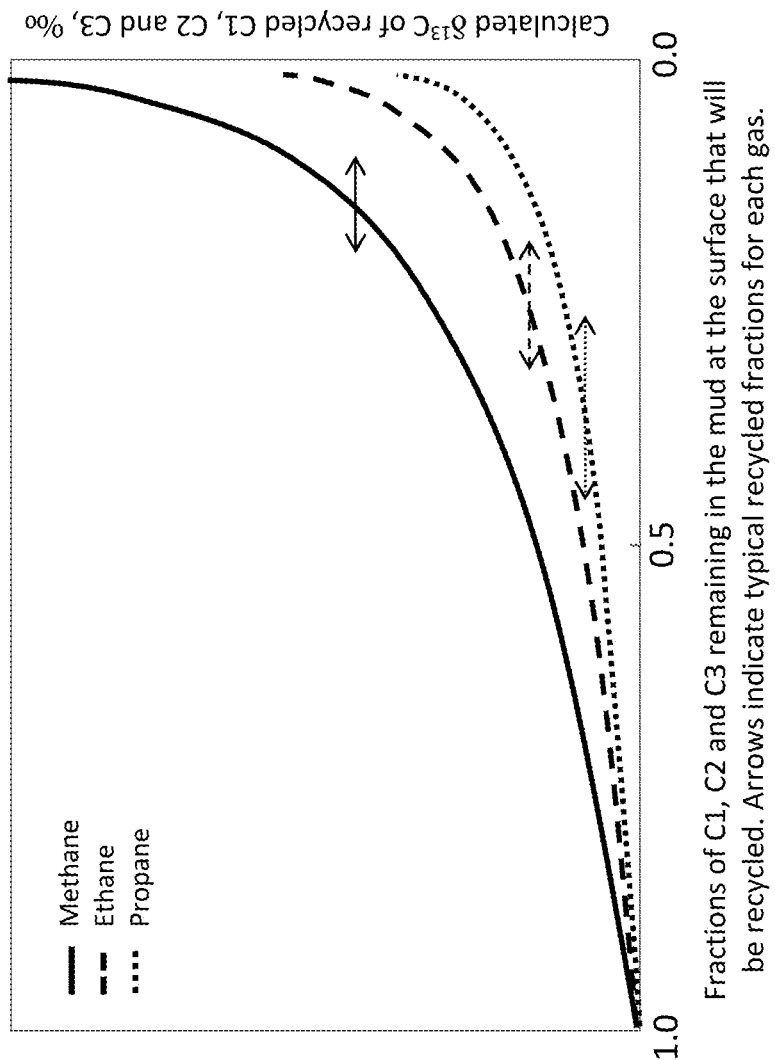
FIG. 8 is a graph showing calculated isotope fractionation of C1, C2 and C3 during degassing from the drilling mud.

Referring now to FIG. 4, shown therein is a diagrammatic representation of another embodiment of a method performed by the processor 80 of the mud gas analyzer 60 to measure the isotopic characteristics of the formation gas using methane (C1) as example. The embodiment depicted in FIG. 4 differs from the embodiment of FIG. 3, in that the mud gas analyzer 60 only measures the sequence of measurements of the isotopic characteristics of the drilling mud gas OUT (e.g., $\delta^{13}C\text{-}C1$) and quantitative OUT concentrations (e.g. C1) is taken by the gas analyzer 62-1 (as shown in block 122) during drilling, and uses experimental measurements taken prior to drilling to correct the reading for the residual gases in the drilling mud 32. As shown in block 140, in the embodiment of FIG. 4 (and also shown in the graph of FIG. 8), experimental measurements to obtain values of the kinetic isotopic fractionation factor (α) of mud degassing are provided. In particular, FIG. 8 shows isotope fractionation of C1, C2 and C3 during degassing from mud and comparisons of relative magnitude. C2 and C3 have higher retentions in drilling mud 32, however calculated isotopic fractionation is smaller due to smaller relative-mass differences between $^{13}$C-containing molecules and $^{12}$C-containing molecules. The graph of FIG. 8 shows exemplary calculation of $\delta^{13}$C fractionation curves based on $\alpha^{13}C_{surface}$ obtained from several field observations.

These methods include (i) observations from past wells drilled with continuous real time (CRT) isotope mud gas logging, (ii) proposed laboratory-based experiments—obtaining extraction efficiency coefficient (EEC) of $^{12}$C and $^{13}$C during lab mud-degassing experiments and (iii) proposed on-site measurements during drilling operation—obtaining EEC of the mud pit (or in general of the surface degassing) on the rig during operation, in static (mud circulation stopped) and dynamic conditions during mud circulation. An exemplary equation used to calculate $\alpha^{13}C\text{-}C1_{surface}$ for methane is shown below:

$$\alpha^{13}C\text{-}C1_{surface} = \{[\ln\{(\delta^{13}C\text{-}C1_{IN}+1000)/(\delta^{13}C\text{-}C1_0+1000)\}/\ln(f_{residual})]+1\}^{-1}$$

where $\delta^{13}C\text{-}C1_0$ refers to initial $\delta^{13}C\text{-}C1$ of the original large methane peak observed in gas OUT, $f_{residual}$—fraction of methane not degassed from mud and recycled as $C1_{IN}$, $\delta^{13}C\text{-}C1_{IN}$ stands for $\delta^{13}C\text{-}C1$ of the recycled portion of methane ($C1_{IN}$).

At block 142, the time that the drilling mud 32 spends degassing at the surface is measured or calculated. At block 144, continuous test measurement of drilling mud gas OUT and drilling mud gas IN fraction of a gas species combined with its isotopic composition will provide information on degree of variability of $\alpha_{surface}$, its range and dependence on drilling operation-related factors (e.g. mud properties, weather, etc.). Such knowledge collected from multiple locations with different types of mud, can stimulate development of predictive real time correction procedure, requiring lower number of time-consuming direct measurements on the rig. For example, for the correction of $\delta_{formation}$ values for i) recycling of mud gas with only gas OUT measurement and ii) the fraction of gas retained in mud before re-injection ($f_{residual}$) would need to be calculated using prior empirical knowledge on (I) the degassing rate ($k_{surface}$) of a gas species from mud on the surface (e.g. mud pit) and (II) isotopic fractionation factor of the mud degassing process ($\alpha_{surface}$). Additionally, CRT measurement of degassing time (t) of each mud portion spent at the surface is required for $f_{residual}$ calculation following decay equation using methane (C1) as an example:

$$C1_{IN(t)} = C1_{OUT(t0)} * e^{-k_{surface}*t}$$

Where $C1_{IN(t)}$ is C1 not degassed out of mud over time t, from the initial concentration $C1_{OUT(t0)}$. Additionally:

$$f_{residual} = C1_{IN(t)}/C1_{OUT(t0)}$$

hence:

$$f_{residual} = e^{-k_{surface}*t} \text{ or } e^{\hat{}}(-k_{surface}*t)$$

Consequently the $\delta^{13}C\text{-}C1_{IN(t)}$ remaining in mud derived from equation for alfa kinetic fractionation factor $\alpha^{13}C\text{-}C1_{surface} = \{[\ln\{(\delta^{13}C\text{-}C1_{IN(t)}+1000)/(\delta^{13}C\text{-}C1_{OUT(t0)}+1000)\}/\ln(f_{residual})]+1\}^{-1}$ is:

$$\delta^{13}C\text{-}C1_{IN(t)} = [(\delta^{13}C\text{-}C1_{OUT(t0)}+1000)*f_{residual}\hat{}(\alpha^{13}C\text{-}C1^{-1}_{surface}-1)]-1000$$

and finally:

$$\delta^{13}C\text{-}C1_{IN(t)} = [(\delta^{13}C\text{-}C1_{OUT(t0)} + 1000) \times e^{\hat{}}((k_{surface}*t)*(1-\alpha^{13}C\text{-}C1^{-1}_{surface}))] - 1000$$

or $$\delta^{13}CC1_{IN(t)} = \left[(\delta^{13}CC1_{OUT(t0)} + 1000) \times e^{k_{surface} \times t \times (1-1/\alpha^{13}CC1_{surface})}\right] - 1000$$

Figure 9:
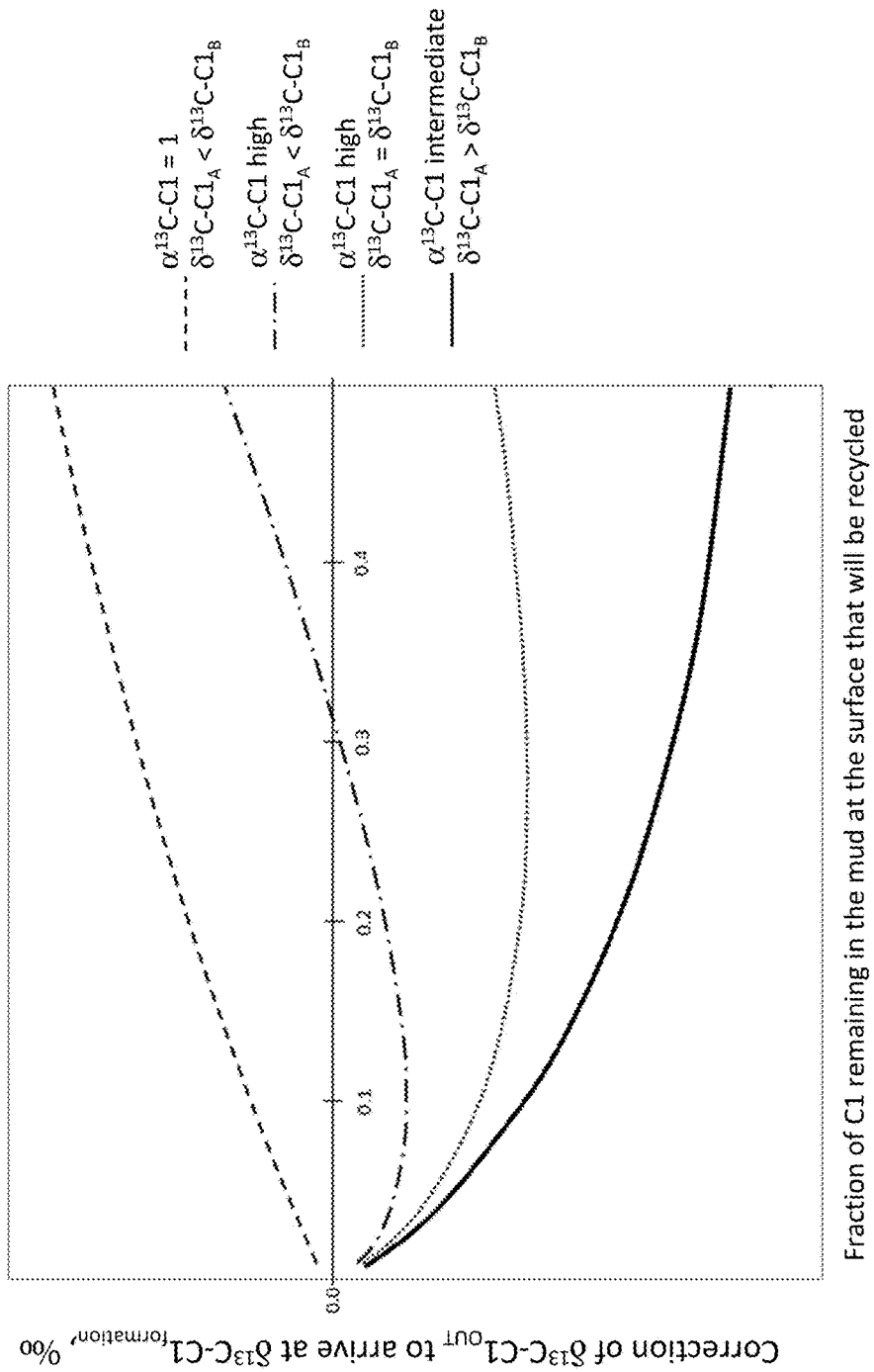
FIG. 9 is a graph showing exemplary results of a sensitivity study of correction factors of $\delta^{13}C\text{-}C1_{OUT}$ to arrive at $\delta^{13}C\text{-}C1_{formation}$ using methane (C1) as an example that have been calculated using the formulas described herein.

Dependence on temperature of $k_{surface}$ and $\alpha_{surface}$ may be analyzed and used to correct $\delta_{formation}$ using CRT temperature reads of drilling mud OUT, drilling mud IN and of atmospheric temperature. Additionally, as $k_{surface}$ and $\alpha_{surface}$ are likely to be affected by any changes in mud properties, it is recommended to re-evaluate such factors during each drilling section. The predictive correction model however, can be further fine-tuned by multiple iterations of deployment of the more robust correction method using direct analysis of OUT and IN gas, as described above. Shown in FIG. 9, is a graph of results from an exemplary sensitivity study on required correction of $\delta^{13}C\text{-}C1$ to arrive at $\delta^{13}C$ of formation C1. Variables considered in this sensitivity study were: fraction of C1 recycled, $\delta^{13}C\text{-}C1$ difference between initially drilled and underlying formations (formation A and formation B), $\alpha^{13}C$ fractionation factor of C1 degassing from mud at the surface 35. In this sensitivity study, the concentration of $C1_{formation}$ was kept constant.

Figure 10:
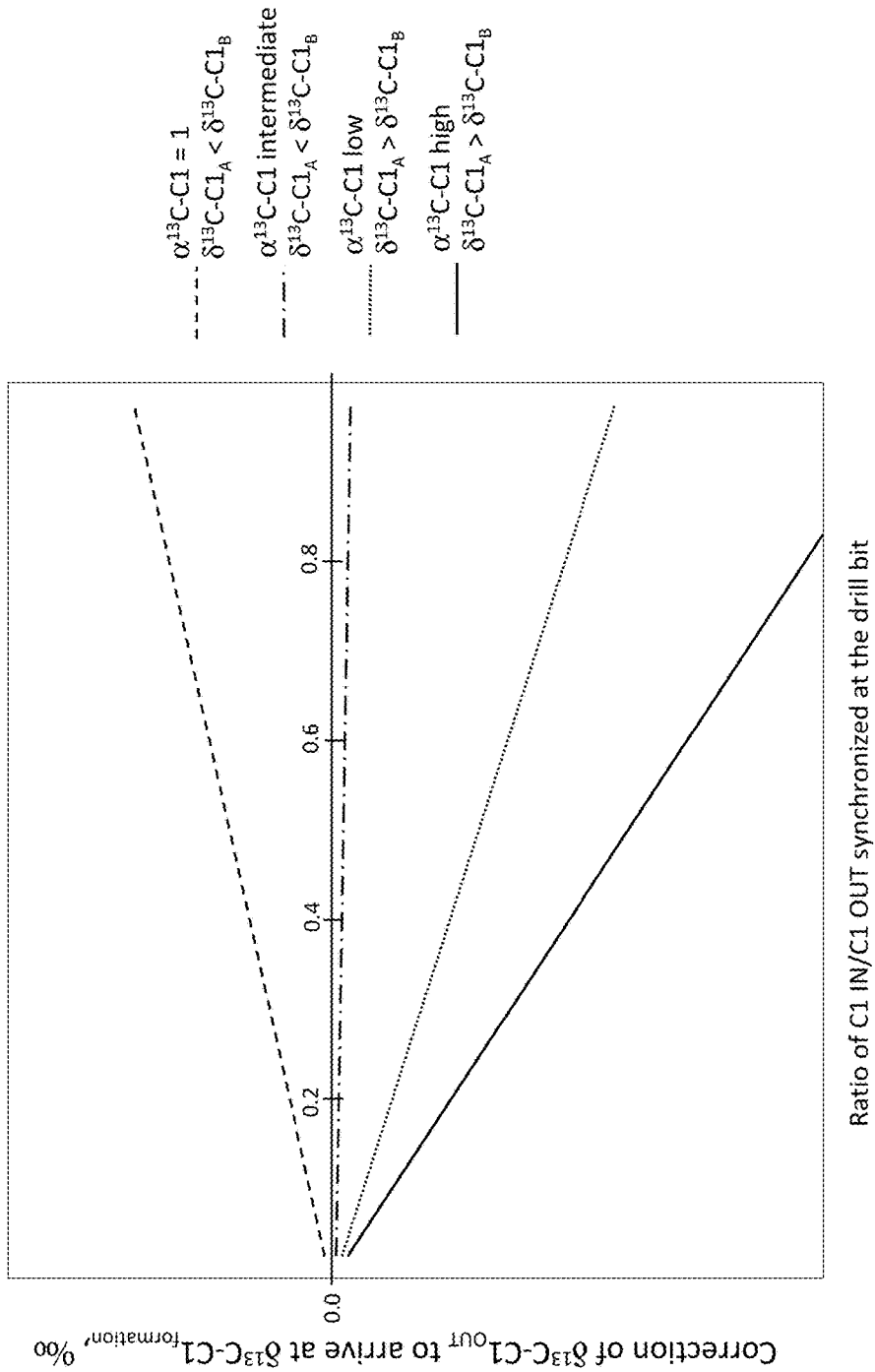
FIG. 10 is a graph showing exemplary results of another sensitivity study on corrections of $\delta^{13}C\text{-}C1_{OUT}$ to arrive at $\delta^{13}C\text{-}C1_{formation}$ using methane (C1) as an example.

Shown in FIG. 10 is a graph showing the results of another exemplary (using C1) sensitivity study on correction of $\delta^{13}C\text{-}C1$ to arrive at $\delta^{13}C$ of formation C1. Variables considered here were: Ratio of C1 IN/C1 OUT synchronized at drill bit, $\delta^{13}C\text{-}C1$ difference between initially drilled and underlying formations (formation A and formation B), $\alpha^{13}C$ fractionation factor of C1 degassing from mud at the surface. In this study, recycled C1 was kept constant at 10%.

Figure 5:
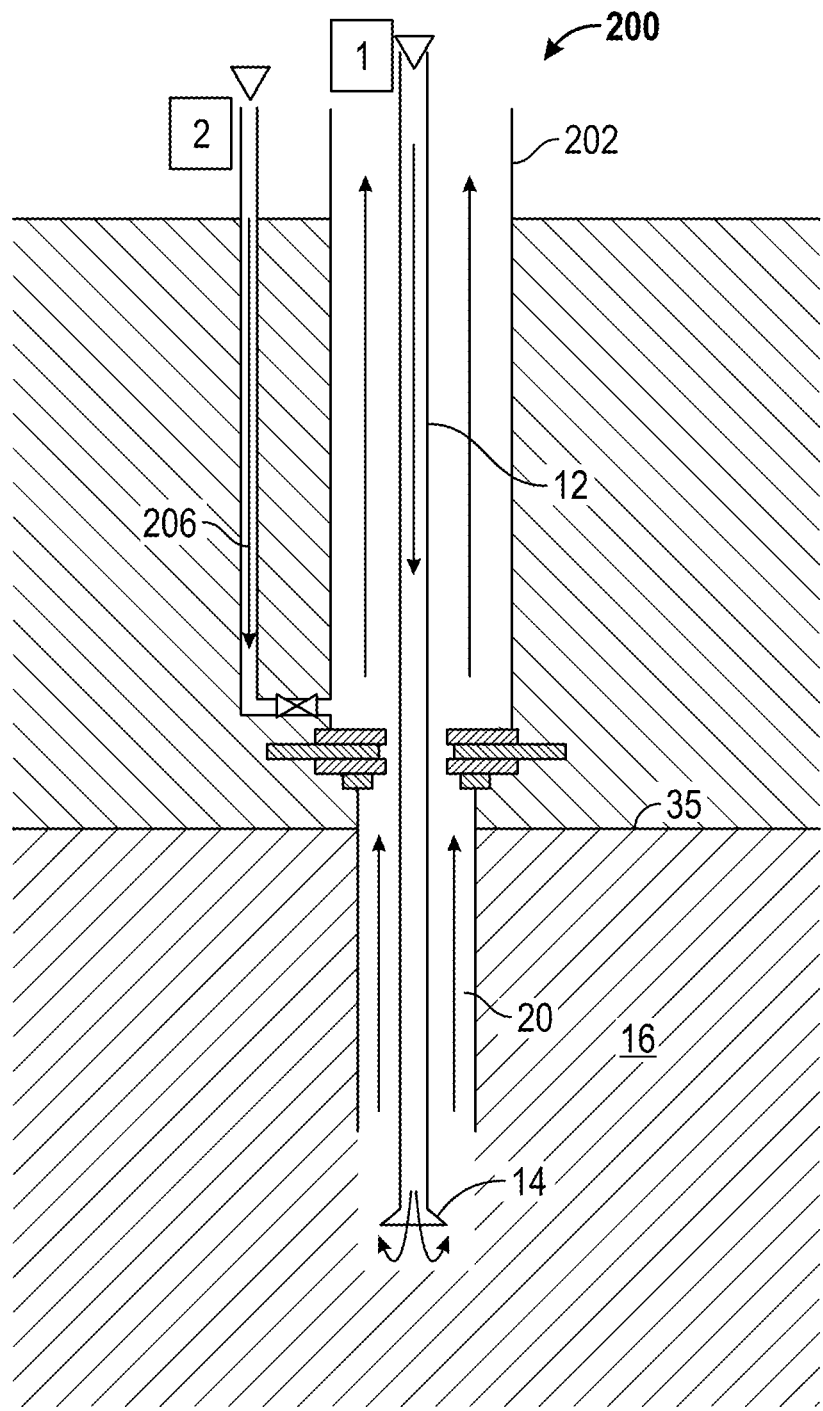
FIG. 5 is a second embodiment of a portion of a well-site system that is similar in construction to the well-site system of FIG. 1, with the exception that the well-site system of FIG. 5 is adapted for deep off-shore operations.
Figure 6:
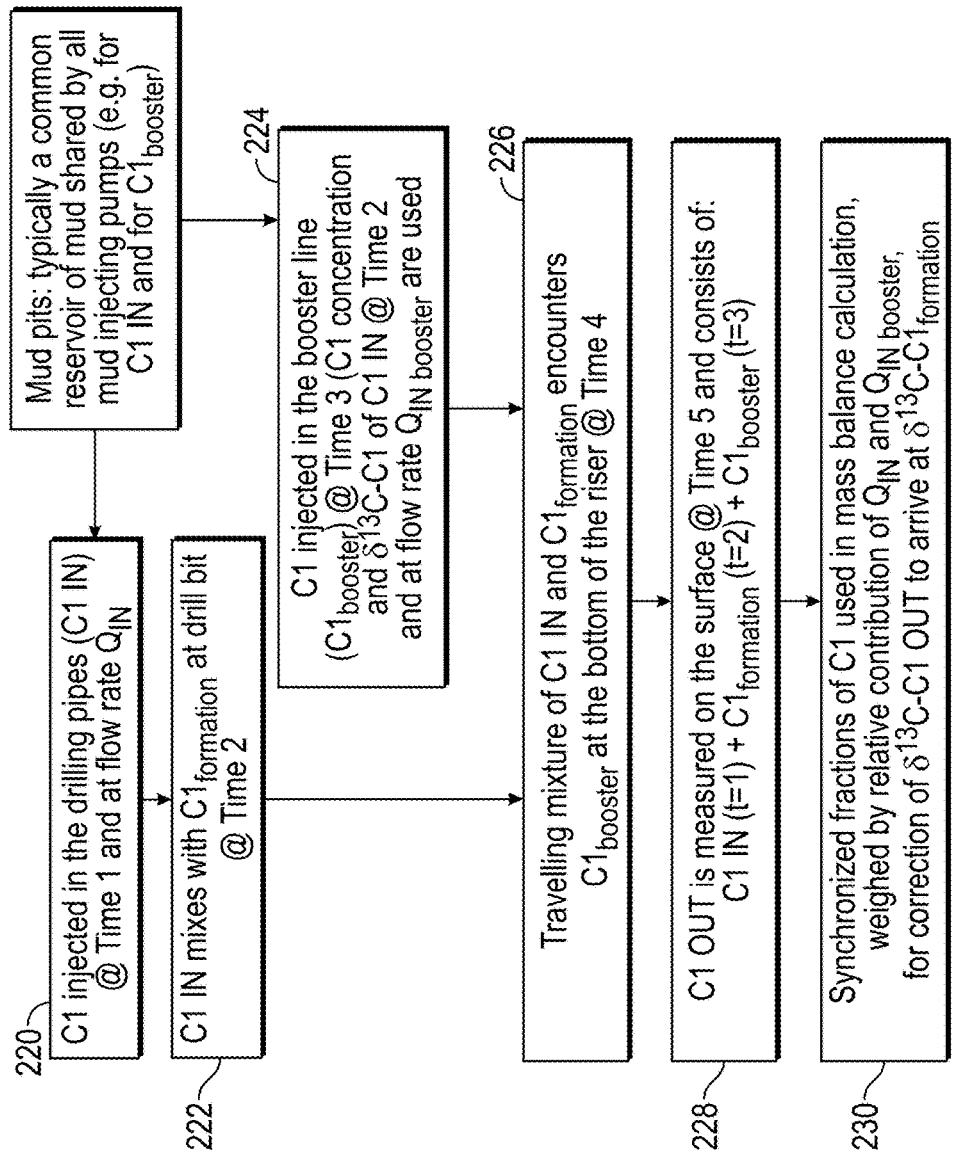
FIG. 6 is a logic flow diagram of yet another embodiment of gas analysis logic that causes a processor to calculate and log isotopic characteristics of gas entering the drilling mud at particular locations of the well within the well-site system of FIG. 5 that is adapted for deep off-shore operations.

Referring to FIGS. 5 and 6, the inventive concepts described herein can also be used where the drilling mud 32 is provided to the wellbore 18 and/or a casing above the wellbore 18 with multiple flow lines, such as when additional drilling mud 32 is provided above the surface 35 of the ocean in off-shore drilling to aid in the collection of the cuttings. Shown in FIG. 5 is a partial schematic diagram of an off-shore well-site system 200 that is constructed in a similar manner as the wellsite system 10, discussed above, with the exception: (1) the drill string 12 passes through a second casing 202 extending from a ship (not shown) to the surface 35 of the geologic formation 16, (2) a booster line 206 fluidly connected to the second casing 202 near the surface 35 of the geologic formation is added to inject drilling mud 32 into the second casing 202 to aid in carrying cuttings to the ship.

In operation, as shown in FIG. 6, drilling mud 32 is injected into the drill string 12 by the mud pump 34 as discussed above at Time 1 at a first flow rate $Q_{IN}$ (as indicated by a block 220). As shown by block 222, the drilling mud 32 having the residual gas composition mixes with the formation gas at the drilling device at a Time 2 that depends upon the flow rate of the drilling mud 32. As shown by block 224, the drilling mud 32 having the residual gas composition is also injected through the booster line 206 at a Time 3, and at a second flow rate $Q_{IN\ booster}$ using another mud pump that may be referred to as a booster pump and whose flow rate may be measured by a second flowmeter. The drilling mud 32 injected through the drill string 12 is going out of the drilling tool 14, carrying drilled rock cuttings and released formation gas to the ship through the annulus 20 and the second casing 202. As shown by block 226, the drilling mud 32 injected through the booster line 206 is mixing at the sea floor, i.e., surface 35, at a Time 4, and their gas content are mixing as well resulting in a new composition. The new composition directly depends on the respective flow rates $Q_{IN}$ and $Q_{IN\ booster}$, gas concentrations and isotopic compositions.

In this scenario, using C1 as an example, C1 OUT is measured on the surface at Time 5 and includes $C1_{IN}$ (t=1)+$C1_{formation}$ (t=2)+$C1_{booster}$ (t=3) as indicated by a block 228. Then, synchronized fractions of C1 are used in a mass balance calculation of $\delta^{13}C\text{-}C1_{formation}$ involves three fractions of C1: $f_{IN}$, $f_{formation}$ and $f_{booster}$. $C1_{booster}$ is portion of C1 not degassed at the surface out of the same mud reservoir as $C1_{IN}$ (typically booster pumps together with other mud flow pumps use the same mud pits). Therefore, C1 concentration and $\delta^{13}C\text{-}C1$ values for $C1_{booster}$ are equal to values of $C1_{IN}$, but at the time of $C1_{booster}$ injection ($\neq C1_{IN}$ injection). Additionally fractions of $C1_{IN}$ and $C1_{IN\ booster}$ may be weighed proportionally to the mud flow IN ($Q_{IN}$) and the booster mud flow ($Q_{IN\ booster}$). Resulting $f_{formation}=1-a*f_{IN}-b*f_{IN\ booster}$, where $a=Q_{IN}/(Q_{IN}+Q_{IN\ booster})$, and $b=Q_{IN\ booster}/(Q_{IN}+Q_{IN\ booster})$. After all three fractions are synchronized for depth and/or well geometry at the bottom of the wellbore 18, as indicated by block 230, $\delta^{13}C\text{-}C1_{formation}$ can be calculated using the mass balance equation:

$$\delta^{13}C\text{-}C1_{formation}=(\delta^{13}C\text{-}C1_{OUT}-a*f_{IN}*\delta^{13}C\text{-}C1_{IN}-b*f_{IN\ booster}*\delta^{13}C\text{-}C1_{IN\ booster})/(1-a*f_{IN}-b*f_{IN\ booster})$$

Additionally, the present disclosure also provides a method of assessment of and correction for the extractor-related isotopic fractionation. Correction for the mud sample degassing process at the degasser itself can be applied to arrive at accurate $\delta_{formation}$. This extractor-correction can be applied by measuring (i) extraction efficiency coefficient (EEC) and (ii) $\alpha_{degasser}$, both for individual gas species. The $\alpha_{degasser}$ will remain constant for a constant PVT degasser but may vary with mud type. However, if different type of degasser is used, again the EEC and $\alpha_{degasser}$ may need to be re-analyzed for every well section and potentially with every change in mud properties.

Models presented here on example of C1 also show that owing to mixing of formation gas with the recycling gas, the cleanest isotopic signature of the formation gas is expected at highest $C1_{formation}$ concentration or lowest C1 IN/C1 OUT ratio, when considering methane (C1) as an example. Thanks to continuous isotope logging, one can select the least affected data points for geochemical interpretation. This contributes to a great advantage over spot sampling (e.g. isotubes). Such spot sampling, not only does not correct for molecular and isotopic recycling, but also may be susceptible to a misrepresentation of the $\delta^{13}C\text{-}C1_{formation}$ depending on a scenario and on which portion of the C1 peak was sampled. With real time isotope logging combined with quantitative C1 concentrations, and isotope recycling correction described herein, it is possible to calculate thermogenic end-member of a C1 peak in a reservoir that exhibits mixing trends with underlying and overlying background C1. Such solution involves a mass balance calculation using C1 concentrations and $\delta^{13}C\text{-}C1$ of the background and peak using a suitable formula, such as:

$$\delta^{13}C\text{-}C1_{thermogenic\ end-member}(\delta^{13}C\text{-}C1_{formation}-f_{background}*\delta^{13}C\text{-}C1_{background})/(1-f_{background})$$

REFERENCES

Bernard, B. B., Brooks, J. M., Sackett, W. M., 1978. Light hydrocarbons in recent Texas continental shelf and slope sediments. Journal of Geophysical Research 83, 4053-4061.

Berner U, Faber E. 1988. Maturity related mixing model for methane, ethane and propane, based on carbon isotopes. Advances in Organic Geochemistry 13, 67-72.

Breviere J, Baer D, Whiticar M, 2008. Device for quantifying the relative contents of two isotopes of at least one specific gaseous constituent contained in a gaseous sample from a fluid, related assembly and process. World Patent WO 2008/017949.

Breviere J, Baer D, Whiticar M. 2009. Device for quantifying the content of at least one gaseous constituent contained in a gaseous sample from a fluid, related assembly and process. World Patent WO 2009/037517.

Breviere J, Evrard J-F. 2006. Module for extracting gas from an underground liquid and installation equipped therewith. U.S. Pat. No. 7,032,444.

Duriez et al. 2002 Method and system for extracting, analyzing and measuring constituents transported by a bore fluid. U.S. Pat. No. 6,443,001.

Faber E, Gerling P, Dumke I. 1988. Gaseous hydrocarbons of unknown origin found while drilling. Organic Geochemistry 13, 875-879.

Frechin N, Breviere J. 2006. Method for determining the content of at least one given gas in a drilling mud, associated device and rig. United States patent application US 2006/0224333 A1.

Jones C, Sofer Z, Drozd RJ. 2005. Method and apparatus for performing rapid isotopic analysis via laser spectroscopy. European Patent Application EP 1508794 A1.

McKinney D, Flannery M, Elshahawi H, Stankiewicz A, Clarke E, Breviere J, Sharma S. 2007. Advanced Mud Gas Logging in Combination With Wireline Formation Testing and Geochemical Fingerprinting for an Improved Understanding of Reservoir Architecture. Society of Petroluem Engineers, Conference Papers, SPE 109861-MS.

Schoen M. 1983. Genetic characterization of natural gases. American Association of Petroleum Geologists Bulletin 67, 2225-2238.

Uehara K, Yamamoto K, Kikugawa T, Yoshida N. 2001. Isotope analysis of environmental substances by a new laser-spectroscopic method utilizing different pathlengths. Sensors and Actuators B 74, 173-178.

Wenger L M, Pottorf R J, Macleod G, Otten G, Dreyfus S, Justwan H. 2009. Drill-bit methamorphism: Recognition and impact on show evaluation. SPE Conference Papers, SPE-125218-MS.

Whiticar M. 1996. Carbon and hydrogen isotope systematics of bacterial formation and oxidation of methane. Chemical Geology 161, 291-314.

Although a few embodiments of the present disclosure have been described in detail above, those of ordinary skill in the art will readily appreciate that many modifications are possible without materially departing from the teachings of the present disclosure. Accordingly, such modifications are intended to be included within the scope of the present disclosure as defined in the claims.

What is claimed is:

1. A mud gas analyzer, comprising:
   a plurality of degassers adapted to extract gas from drilling mud passing through a flow path formed at least partially by a drill string within a well and an annulus positioned between an exterior surface of the drill string and a formation surrounding the well at a well-site, wherein the plurality includes a first degasser and a second degasser, the first degasser adapted to extract gas passing through the flow path upstream of the drill string, and the second degasser adapted to extract gas passing through the flow path downstream of the annulus and downstream with respect to the first degasser;
   at least one gas analyzer, adapted to analyze the gas extracted by the plurality of degassers and generate a sequence of signals indicative of ratios of isotopes of gas species of gas extracted from the drilling mud; and
   a computer system including a processor adapted to execute logic to cause the processor to, receive the sequence of signals, and to calculate and log isotopic characteristics of gas entering the drilling mud at particular locations of the well.

2. The mud gas analyzer of claim 1, wherein the computer system is coupled to the at least one gas analyzer and a flow meter.

3. The mud gas analyzer according to claim 2, where the computer system accesses information indicative of a flow of the drilling mud, a geometry of the well and a geometry of the tool string or any other source providing particular locations of the well of mixing gases, and wherein the processor calculates and logs isotopic characteristics of gas entering the drilling mud at particular locations of the well using the information indicative of the flow of the drilling mud, the geometry of the well and the geometry of the tool string or any other source providing particular locations of the well of mixing gases.

4. The mud gas analyzer of claim 1, wherein the at least one gas analyzer is at least one of a spectrophotometer and a gas chromatograph-isotope ratio mass spectrometer or any other technology able to provide measurement of relative concentrations of isotopes of at least one element within one or more gas species.

5. The mud gas analyzer of claim 1, wherein the at least one gas analyzer is a plurality of gas analyzers including a first gas analyzer adapted to analyze gas extracted by the first degasser, and further comprising a second gas analyzer adapted to analyze gas extracted from the second degasser, and wherein signals to be generated by the first gas analyzer are indicative of a first level of retention of gas species of the gas in the drilling mud prior to reinjection of the drilling mud into the drill string, and signals to be generated by the second gas analyzer are indicative of a second level of retention of the gas species of the gas in the drilling mud upon exiting from the annulus.

6. The mud gas analyzer of claim 5, wherein the computer system analyzes the sequence of signals to determine an isotopic composition of a gas species with logic indicative of $\delta_{formation} = (\delta_{OUT} - f_{IN} * \delta_{IN}) / f_{formation}$ where $\delta_{formation}$ is the isotopic composition of the gas entering the drilling mud at particular locations of the well, $\delta_{OUT}$ is the isotopic composition of the gas in the drilling mud upon exiting from the annulus, $\delta_{IN}$ is the isotopic composition of the gas in the drilling mud prior to reinjection of the drilling mud into the drill string, $f_{IN}$ is a fraction of the gas species transported out that is not coming from the formation, but is recycled gas; and $f_{formation} = 1 - f_{IN}$.

7. The mud gas analyzer according to claim 1, wherein the gas analyzer is adapted to separately analyze gas extracted by the first degasser and the second degasser and to generate signals indicative of a first level of retention of gas species of the gas in the drilling mud prior to reinjection of the drilling mud into the drill string, and to generate signals indicative of a second level of retention of the gas species of the gas in the drilling mud upon exiting from the annulus.

8. The mud gas analyzer according to claim 1, where the flow path is a first flow path having a first section and a second section, and further comprising a second flow path separate from the first section of the first flow path, the second flow path being coextensive with the second section of the first flow path, and wherein the processor is adapted to execute logic to cause the processor to access information indicative of the geometry of the well, the geometry of the tool string or any other source providing depth at which mixing gases are synchronized, and to calculate and log isotopic characteristics of gas entering the drilling mud at particular locations of the well using flow rates of the first and second paths.

9. The mud gas analyzer of claim 8, where the computer system analyzes the sequence of signals to determine an isotopic composition of a gas species with logic indicative of $\delta_{formation} = (\delta_{OUT} - a * f_{IN} * \delta_{IN} - b * f_{IN\ booster} * \delta_{IN\ booster})/(1 - a * f_{IN} - b * f_{IN\ booster})$, wherein a mass balance calculation of $\delta_{formation}$ involves three fractions of the gas species: $f_{IN}$, $f_{formation}$ and $f_{IN\ booster}$; $f_{IN\ booster}$ is a portion of the gas species not degassed at the surface out of a same mud reservoir as $f_{IN}$; and a and b are relative contributions first and second flow rates described in claim 8.

10. A mud gas analyzer, comprising:
   at least one degasser adapted to extract gas from drilling mud passing through a flow path formed at least partially by a drill string within a well and an annulus positioned between an exterior surface of the drill string and a formation surrounding the well at a well-site;
   at least one gas analyzer, adapted to analyze the gas extracted by the plurality of degassers and generate a sequence of signals indicative of ratios of isotopes of gas species of gas extracted from the drilling mud; and a computer system including a processor adapted to execute logic to cause the processor to, receive the sequence of signals, and to calculate and log isotopic characteristics of gas entering the drilling mud at particular locations of the well, wherein the computer system uses data indicative of a predetermined rate of degassing of gas from the drilling mud, and one or more predetermined kinetic isotopic fractionation factor to calculate and log isotopic characteristics of gas entering the drilling mud at particular locations of the well.

11. The mud gas analyzer of claim 10, wherein the computer system analyzes the sequence of signals to determine an isotopic composition of a gas species with logic indicative of $\delta_{IN\ (t)} = [\delta_{OUT\ (t0)} + 1000)*e^{\wedge}((k_{surface}* t)*(1-\alpha^{-1}_{surface}))] - 1000$ where $k_{surface}$ is the degassing rate of the gas species from mud on the surface (e.g. mud pit), t is exposure time of a volume of mud to the surface degassing process starting at t0 when mud from which $\delta^{13}_{OUT\ (t0)}$ was measured, and $\alpha_{surface}$ is the isotopic fractionation factor of the mud degassing process.

12. A well-site system, comprising:
a drill string having a drilling tool positioned in a formation to bore a well through the formation thereby creating an annulus between an exterior surface of the drill string and the formation, the well having an entrance;
a container containing drilling mud and being fluidly connected to the entrance of the well to receive drilling mud from the well;
a mud pump having an inlet receiving drilling mud from the container, and an outlet injecting drilling mud into the drill string through a flow path formed at least partially by the drill string and the annulus;
a mud gas analyzer according to claim 1.

13. The well-site system of claim 12, wherein the mud gas analyzer includes a plurality of degassers, wherein the plurality includes a first degasser and a second degasser, the first degasser adapted to extract gas passing through the flow path upstream of the drill string, and the second degasser adapted to extract gas passing through the flow path downstream of the annulus and downstream with respect to the first degasser and wherein the at least one gas analyzer is a plurality of gas analyzers including a first gas analyzer adapted to analyze gas extracted by the first degasser, and further comprising a second gas analyzer adapted to analyze gas extracted from the second degasser, and wherein signals to be generated by the first gas analyzer are indicative of a first level of retention of gas species of the gas in the drilling mud prior to reinjection of the drilling mud into the drill string, and signals to be generated by the second gas analyzer are indicative of a second level of retention of the gas species of the gas in the drilling mud upon exiting from the annulus.

14. The well-site system according to claim 12, wherein the computer system analyzes the sequence of signals to determine an isotopic composition of a gas species with logic indicative of $\delta_{formation} = (\delta_{OUT} - f_{IN}*\delta_{IN})/f_{formation}$ where $\delta_{formation}$ is the isotopic composition of the gas entering the drilling mud at particular locations of the well, $\delta_{OUT}$ is the isotopic composition of the gas in the drilling mud upon exiting from the annulus, $\delta_{IN}$ is the isotopic composition of the gas in the drilling mud prior to reinjection of the drilling mud into the drill string, $f_{IN}$ is a fraction of the gas species transported out that is not coming from the formation, but is recycled gas; and $f_{formation} = 1 - f_{IN}$.

15. The well-site system according to claim 12, wherein the computer system uses data indicative of a predetermined rate of degassing of gas from the drilling mud, time of degassing of particular mud volume, and one or more predetermined kinetic isotopic fractionation factor to calculate and log isotopic characteristics of gas entering the drilling mud at particular locations of the well.

16. One or more non-transitory computer readable medium storing processor executable code that when executed by one or more processors of a computer system cause the one or more processor to:
receive information indicative of a geometry of a well, and a geometry of a tool string within the well, and a flow rate of drilling mud from at least one of a communication device and input device of the computer system or receive information from any other source providing particular locations of the well at which mixing of fractions of a gas species occurred
receive a sequence of signals indicative of ratios of isotopes of a gas species of gas extracted from a drilling mud from the at least one of the communication device and the input device of the computer system, and
calculate and log isotopic characteristics of gas entering the drilling mud at particular locations of the well,
wherein the signals are indicative of a first level of retention of gas species in the drilling mud prior to reinjection of the drilling mud into the drill string, and are also indicative of a second level of retention of gases in the drilling mud upon exiting from an annulus; and
wherein the processor executable code, when executed by one or more processors of the computer system, cause the one or more processor to analyze the sequence of signals to determine an isotopic composition of a gas species with logic indicative of $\delta_{formation} = (\delta_{OUT} - f_{IN}*\delta_{IN})/f_{formation}$ where $\delta_{formation}$ is the isotopic composition of the gas entering the drilling mud at particular locations of the well, $\delta_{OUT}$ is the isotopic composition of the gas in the drilling mud upon exiting from the annulus, $\delta_{IN}$ is the isotopic composition of the gas in the drilling mud prior to reinjection of the drilling mud into the drill string, $f_{IN}$ is a fraction of the gas species transported out that is not coming from the formation, but is recycled gas; and $f_{formation} 1 - f_{IN}$.

17. One or more non-transitory computer readable medium storing processor executable code that when executed by one or more processors of a computer system cause the one or more processor to:
receive information indicative of a geometry of a well, and a geometry of a tool string within the well, and a flow rate of drilling mud from at least one of a communication device and input device of the computer system or receive information from any other source providing particular locations of the well at which mixing of fractions of a gas species occurred
receive a sequence of signals indicative of ratios of isotopes of a gas species of gas extracted from a drilling mud from the at least one of the communication device and the input device of the computer system, and
calculate and log isotopic characteristics of gas entering the drilling mud at particular locations of the well,
wherein the processor executable code, when executed by one or more processors of the computer system, cause the one or more processor to use data indicative of a predetermined rate of degassing of gas from the drilling mud, and one or more predetermined kinetic isotopic fractionation factor to calculate and log isotopic characteristics of gas entering the drilling mud at particular locations of the well.

* * * * *